US012616566B2

(12) United States Patent
Holmström et al.

(10) Patent No.: US 12,616,566 B2
(45) Date of Patent: May 5, 2026

(54) ADAPTIVE MULTIFOCAL DIFFRACTIVE OCULAR LENS

(71) Applicant: VSY Biyoteknoloji ve Ilac Sanayi A.S., Tuzla (TR)

(72) Inventors: Sven Thage Sigvard Holmström, Tuzla (TR); Amin Tabatabaei Mohseni, Tuzla (TR); Efe Can, Tuzla (TR)

(73) Assignee: VSY BIYOTEKNOLOJI VE ILAC SAN. A.S., Istanbul (TR)

( * ) Notice: Subject to any disclaimer, the term of this patent is extended or adjusted under 35 U.S.C. 154(b) by 314 days.

(21) Appl. No.: 18/547,035

(22) PCT Filed: Feb. 19, 2021

(86) PCT No.: PCT/TR2021/050154
§ 371 (c)(1),
(2) Date: Aug. 18, 2023

(87) PCT Pub. No.: WO2022/177517
PCT Pub. Date: Aug. 25, 2022

(65) Prior Publication Data
US 2024/0307170 A1      Sep. 19, 2024

(51) Int. Cl.
*A61F 2/16*          (2006.01)
*G02C 7/04*          (2006.01)

(52) U.S. Cl.
CPC .......... *A61F 2/1618* (2013.01); *A61F 2/1654* (2013.01); *G02C 7/044* (2013.01); *G02C 2202/20* (2013.01)

(58) Field of Classification Search
CPC ................. A61F 2/1618; A61F 2/1654; A61F 2002/1681; G02C 7/024; G02C 7/028; G02C 7/044; G02C 7/06; G02C 2202/20
See application file for complete search history.

(56) References Cited

U.S. PATENT DOCUMENTS

| | | | | |
|---|---|---|---|---|
| 8,556,416 B2 * | 10/2013 | Lawu | ................... | G02B 5/1895 |
| | | | | 623/6.31 |
| 2020/0209649 A1 * | 7/2020 | Holmström | ............ | G02C 7/024 |
| 2021/0369445 A1 * | 12/2021 | Chiu | ..................... | A61F 2/1618 |

FOREIGN PATENT DOCUMENTS

| | | | |
|---|---|---|---|
| EP | 3 435 143 A1 | 1/2019 | |
| WO | WO 2011/092169 A1 | 8/2011 | |

(Continued)

OTHER PUBLICATIONS

International Search Report, dated Nov. 22, 2021, pp. 1-5, issued in International Patent Application No. PCT/TR2021/050154, European Patent Office, Rijswijk, the Netherlands.

(Continued)

*Primary Examiner* — Nelson M Rosario
(74) *Attorney, Agent, or Firm* — Crowell & Moring LLP

(57)          ABSTRACT

An ophthalmic multifocal lens providing far, intermediate, and near vision having a light transmissive body with an optical axis and a refractive baseline extending over part of the lens body; further having a first portion coinciding with a central area of the lens body and a multifocal second portion extending concentrically radially; the second portion further comprising a symmetric multifocal diffractive grating superpositioned onto the baseline, covering a portion of the lens, its shape and resulting light intensity distribution changing with distance to optical axis, the first portion being substantially concave, connected to the ridge of the grating that is closest to the optical axis and provides a dominant optical power between intended far and intermediate powers; configured to have an energy ratio intended for far vision to energy intended for near vision being lower for predetermined aperture(s).

14 Claims, 14 Drawing Sheets

(56)  References Cited

FOREIGN PATENT DOCUMENTS

Figure 3:
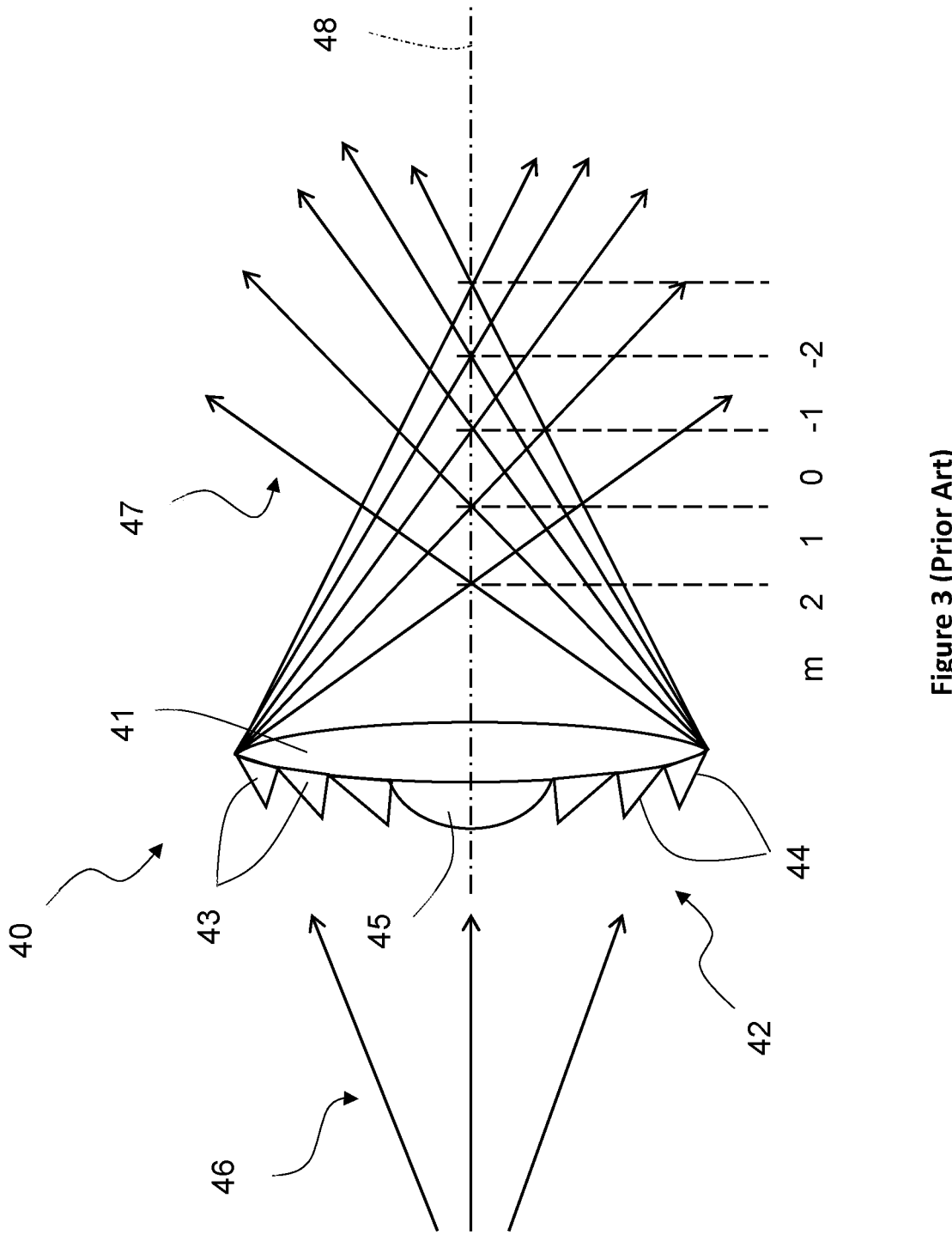

| WO | WO 2017/192333 A1 | 11/2017 |
| WO | WO 2021/089178 A1 | 5/2021 |

OTHER PUBLICATIONS

Written Opinion of the International Searching Authority, dated Nov. 22, 2021, pp. 1-7, issued in International Patent Application No. PCT/TR2021/050154, European Patent Office, Rijswijk, the Netherlands.
International Preliminary Report on Patentability, dated May 10, 2023, pp. 1-8, issued in International Patent Application No. PCT/TR2021/050154, European Patent Office, Munich, Germany.
Gori, F., et al., "Analytical derivation of the optimum triplicator," dated Dec. 1, 1998, pp. 13-16, Optics Communications, vol. 157, No. 1-6, Elsevier, Amsterdam, NL XP004150691.

* cited by examiner

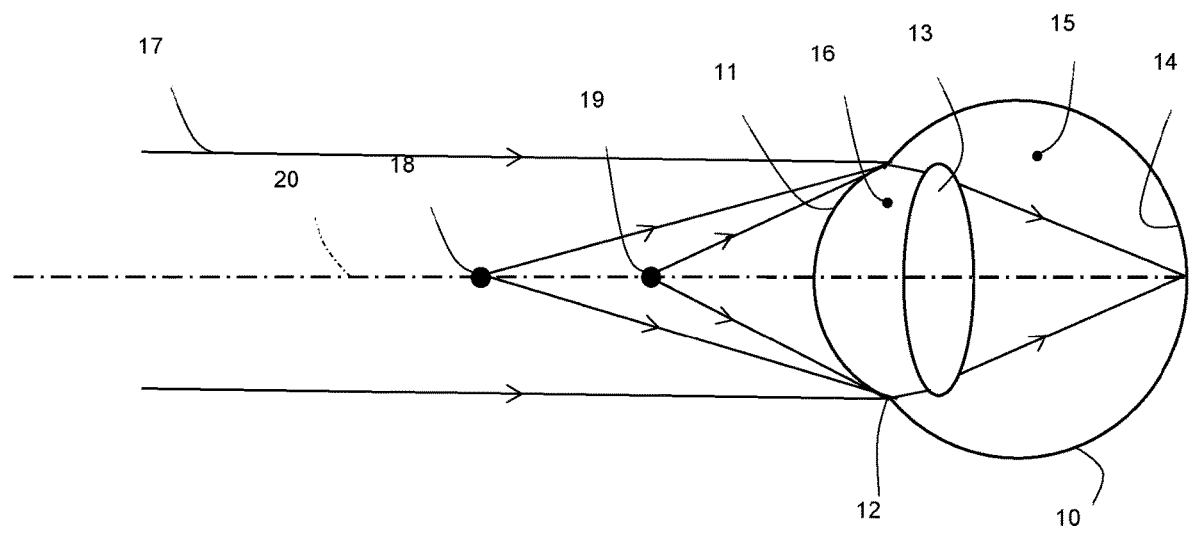
Figure 1 (Prior Art)
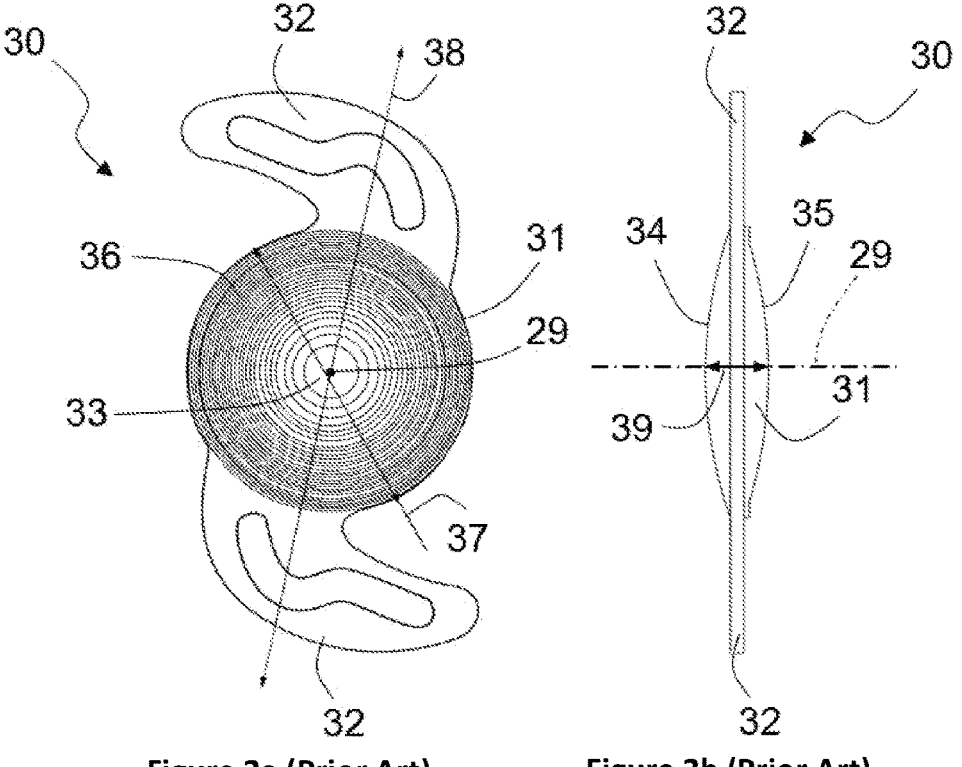
Figure 2a (Prior Art)    Figure 2b (Prior Art)

55

56

54

53

51

52

51

53

52

50

ADAPTIVE MULTIFOCAL DIFFRACTIVE OCULAR LENS

CROSS-REFERENCE TO RELATED APPLICATIONS

This application is the U.S. National Stage application of PCT application no. PCT/TR2021/050154, filed on Feb. 19, 2021, titled AN ADAPTIVE MULTIFOCAL DIFFRAC- TIVE OCULAR LENS, designating the United States, the contents of which are incorporated herein by reference in their entirety.

TECHNICAL FIELD OF THE PRESENT INVENTION

The present disclosure generally relates to ophthalmic lenses and, more specifically, to ophthalmic contact and intra-ocular multifocal lenses, the multifocality being pro- vided by a diffractive structure that is arranged so as to best serve human vision over different pupil sizes.

BACKGROUND OF THE PRESENT INVENTION

Diffractive lenses for ophthalmological applications are constructed as hybrid lenses with a diffractive pattern added onto a refractive body. Often one side of the lens is purely refractive, while the other side has a diffractive grating superpositioned over a refractive base line. The refractive baseline can be spherical, or alternatively have an aspherical shape of sorts. A high order monofocal diffractive pattern can also function as a purely refractive shape. The diffractive part can in general be applied to any of the two sides of the lens, since when a diffractive pattern is to be combined with a refractive surface with some special feature it generally does not matter if they are added to the same side or if one is added to a first side and the other to a second side of the lens. Concurrently, two diffractive patterns may be com- bined either by super positioning on one side, or by adding them on separate sides in an overlapping fashion. The optical power of the lens for a specific diffraction order can be calculated by addition of the refractive base power and the optical power of that diffraction order.

In the anatomy of the eye, light passes through an opening within the iris, called pupil, before reaching the lens and being focused onto the retina. The size of the pupil is governed by the muscles of the iris, so that it rapidly constricts the pupil when exposed to bright light and expands (dilates) the pupil in dim light. The pupillary aperture also narrows when focusing on close objects and dilates for more distant viewing. At its maximum contrac- tion, the adult pupil may be less than 1 mm in diameter, and it may increase up to 10 times to its maximum diameter. The size of the human pupil may also vary as a result of age, disease, trauma, or other abnormalities within the visual system, including dysfunction of the pathways controlling pupillary movement.

Based on the pupillary response in combination with the specific response of cones and rods in the eye's retina, three main modes of eye function under different illuminance levels ($cd/m^2$) are observed: photopic (bright light), scotopic (low light conditions), and mesopic (intermediary). The brightness level of the observed object, the background and surroundings determine the activity of rods and cones by retinal illuminance level (light intensity).

Additionally, the visual system is more sensitive to light coming in through the center of the eye pupil than to light entering from the periphery of the pupil. This is called the Stiles-Crawford Effect of the first kind (SCE-I), also known as the "directional sensitivity of the retina", describes the angular dependence of retinal sensitivity. Axial light rays that enter the pupil near its center, which are parallel to retinal receptors, are more effective than off-axis light oblique rays, which enter the pupil near its margins. There- fore, light passing through the periphery of the pupil is less efficient at stimulating vision than light passing near the center of the pupil (i.e., axial light forms sharper images than off-axis light) and hence increases the depth of focus (refer- ring to: W. Fink and D. Micol, "computer-based simulation of visual perception under various eye defects using Zernike polynomials," J. Biomed. Opt., vol. 11, no. 5, p. 054011, 2006.). The SCE can significantly improve defocused image quality and defocused vision, particularly for tasks that require veridical phase perception (referring to: X. Zhang, M. Ye, A. Bradley, and L. Thibos, "Apodization by the Stiles-Crawford effect moderates the visual impact of retinal image defocus," J. Opt. Soc. Am. A, vol. 16, no. 4, p. 812, 1999).

Note that a diffraction grating that functions as a lens has a pitch that in absolute terms varies with the radius. The pitch depends on the refractive index, the design wave- length, and the optical power of the first diffraction order. The pitch is determined so that the optical path difference (OPD) through the lens to the focal point of the first diffraction order has a difference of exactly one wavelength per period. To show the periodicity of a diffraction grating one will often plot the diffractive lens profile versus the square of the radius. When plotted like this the periods (grating pitch) are equidistant, more exactly the period pitch in $r^2$-space is $2\lambda/D$, where $\lambda$ is the design wavelength and D the optical diffractive power of the first order in diopters. This forms the basis for well-formed, phase-matched dif- fractive lenses.

The term diffractive lens is sometimes used for the well-known Fresnel lenses. A Fresnel lens consists of con- centric zones with vertical steps in the zone junctures. The zones in a Fresnel lens are often of equal width and the optical properties of each zone can be analyzed with refrac- tive theory. However, the diffractive lenses discussed here are lenses which require diffractive analysis.

The most well-researched type of diffraction lens proper is the monofocal phase-matched Fresnel lens as taught by Rossi et al. in their 1995 study titled "Refractive and diffractive properties of planar micro-optical elements". This type of lens makes use of a sawtooth diffractive unit cell and a step height corresponding to a phase modulation of exactly $2\pi$.

It is often desired to provide more than one focal point. For ophthalmic lenses it can be advantageous to provide e.g., far vision and near vision simultaneously. The most light- efficient lens possible for providing two focal points uses a sawtooth profile similar to the phase matched Fresnel described above, but with a decreased height. The highest possible diffraction efficiency for such a lens is close to 81%. For diffractive lenses optimized for more than two focal points sawtooth patterns are not the most efficient and, as will be discussed below, higher diffraction efficiencies are possible.

In recent years it has become increasingly common with lenses providing three distinct focal point, often far, inter- mediate, and near vision.

PCT/EP2019/080758 describes a way to construct a multifocal lens combining a monofocal central zone, providing far vision only, and a symmetric multifocal grating. That document discusses in great detail how to combine a monofocal center zone with a symmetric diffraction grating to achieve as high light efficiency as possible. It also provides a description on how to achieve a desired intensity distribution for one aperture. The addition of a purely monofocal central zone decreases, however, the total light efficiency compared to a lens with a highly efficient grating of the whole lens surface.

WO2020053864A1 discloses a multifocal lens utilizing a symmetric diffractive grating with technically five focal points. Near vision is dominating at apertures of about 2 mm and smaller. Additionally, the peak-to-peak height of the diffractive grating is higher than what is desirable. Measured at a 2 mm aperture the lens, as presented, behaves as a bifocal lens with two rather broad peaks, and at 3 mm it behaves substantially as a trifocal lens.

The vast majority of ophthalmic diffractive trifocal lenses make use of sawtooth profiles. Combining sawtooth profiles of two bifocal diffractive lenses to achieve trifocality is known in the art. This results in diffractive lenses with the usable orders arranged asymmetrically with respect to the $0^{th}$ order e.g., a trifocal lens might make use of orders 0, +1, and +2 orders or 0, +2, and +3. In U.S. Pat. No. 9,320,594, a diffractive trifocal lens is disclosed wherein the optical thickness of the surface profile changes monotonically with radius within each zone, while a distinct step in optical thickness at the junction between adjacent zones defines a step height. The step heights for respective zones may differ from one zone to another periodically so as to tailor diffraction order efficiencies of the optical element wherein the step heights may alternate between two values. In EP 2377493, a method of manufacturing an aphakic intraocular lens capable of ensuring every multi-focusing effect more securely, while reducing the impact of aperture changes and lens eccentricity is suggested. EP 2503962 discloses an intraocular lens including an anterior surface and a posterior surface and having a substantially antero-posterior optical axis wherein one of these anterior and posterior surfaces includes a first diffractive profile forming at least one first diffractive focal point of order +1 on said optical axis, and a second diffractive profile forming a second diffractive focal point of order +1, said two diffractive focal points are distinct and at least one portion of said second diffractive profile is superposed to at least one portion of the first diffractive profile. It further describes how so called apodization of a sawtooth diffraction grating can be used to increase relative intensity of the far vision with increasing aperture. When discussing apodization with regards to diffractive lenses it is understood to refer to a diffractive pattern depth that is decreasing with increasing aperture. WO2019130030A1 describes the of apodization as well as reversed apodization of sawtooth-based diffractive lenses, referring to profile height that is increasing with increasing aperture, to decrease and increase, respectively, the relative intensity to far vision. The combination of these two concepts is referred to as cross apodization. U.S. Pat. No. 9,223,148 proposes a lens with more than two powers, one of which is refractive and one other diffractive in the least. U.S. Pat. No. 5,017,000 suggests a multiple focal point profiled phase plate having a plurality of annular concentric zones spaced according to the formula r(k)=sqrt(constant×k) where r(k) is the zone radii and k is a zone; in which a repetitive step is incorporated in the profile and has an optical path length greater or less than one-half wavelength.

One of the prior art publications in the technical field of the present invention may be referred to as EP 3435143, teaches an ophthalmic multifocal diffractive lens comprising focal points for near, intermediate, and far vision. The lens comprises a light transmissive lens body providing a refractive focal point, and a periodic light transmissive diffraction grating, extending concentrically over at least part of a surface of the lens body and providing a set of diffractive focal points. The diffraction grating is designed to operate as an optical wave splitter, the refractive focal point providing the focal point for intermediate vision and the diffractive focal points providing the focal points for near and far vision. The diffraction grating has a phase profile arranged for varying a phase of incident light at the lens body optimizing overall efficiency of light distribution in the refractive and diffractive focal points. The orders of this lens are arranged symmetrically around the $0^{th}$ order and operates in at least the −1, 0, and +1 orders.

Diffractive lenses with sharp transitions in the diffraction profile, including e.g. lenses with sawtooth profiles or binary profiles, give rise to machining difficulties and, for a finished lens, scattering of light, increased incidence of several unwanted optical phenomena such as stray light and glare i.e. the difficulty of seeing in the presence of bright light such as direct or reflected sunlight or artificial light such as car headlamps at night, and halo effects i.e. white or colored light rings or spots seen at dim light, i.e. under mesopic conditions. Diffractive lenses without sharp transitions are better performing with respect to these issues and also have higher potential diffraction efficiency, at the very least for multifocal lenses with an odd number of focal points. It has also been suggested that sinusoidal or smooth diffractive profiles are more biocompatible compared to sawtooth profiles because of reduction in the debris precipitation effect, as explained in Osipov et al. in their 2015 study "Application of nanoimprinting technique for fabrication of trifocal diffractive lens with sine-like radial profile" as published in *Journal of biomedical optics* 20, no. 2 (2015): 025008.

According to the teaching of WO2019020435, it is known that the light distribution in the focal points of an ophthalmic lens comprising a diffraction grating having a continuous periodic phase profile function and usable orders symmetrically arranged around the $0^{th}$ order is tunable over a relatively large intensity range, by modulating one or both of the arguments and amplitude of the phase profile function as a function of the radius or radial distance to the optical axis of the lens body. A trifocal lens known in the art was put forth in the past few years, with respect to teachings of EP 20170183354 and aforementioned WO 2019020435 which comprise a trifocal lens that operates in the −1, 0, and +1 orders. A general approach to construct a lens is also known from the teaching of U.S. Pat. No. 5,017,000. The resulting diffractive lens is a diffractive lens operating in the 0, +1, and +2 orders.

According to the teaching of WO 2019020435 a trifocal lens can be constructed by starting from a linear phase grating optimized for diffraction efficiency and an equal light distribution between usable diffraction orders. Linear phase gratings have been researched and developed with the intent of creating beam splitters. The general theory of optimization of linear phase gratings is taught in Romero and Dickey's 2007 study titled "Theory of optimal beam splitting by phase gratings. I. One-dimensional gratings" in Journal of the Optical Society of America Vol. 24, No. 8 (2007) p. 2280-2295. The existing literature on diffractive phase grating has focused on finding optimal solution, meaning maximized diffraction efficiency, for the case of equal intensity distribution among a certain number of orders.

Because of reasons given above it is often advantageous to use multifocal, hybrid lenses utilizing smooth diffractive gratings utilizing both positive and negative diffraction orders. However, such lenses that exist in the prior art have several limitations.

A feature often discussed and desired in multifocal lenses providing far, intermediate, and near vision is to provide a relatively even intensity distribution for mesopic conditions while providing a much stronger relative intensity for far vision for the larger pupils available in scotopic conditions. With sawtooth multifocal diffractive lenses this is often provided with the help of apodization, which in this context refers to a diffractive grating with decreasing height with increasing radius, as taught in Davison, J. A., & Simpson, M. J. (2006). History and development of the apodized diffractive intraocular lens. *Journal of Cataract & Refractive Surgery*, 32(5), 849-858. Generally, in diffractive multifocal lenses the height of the grating can be reduced (increased) to increase (reduce) the intensity of the refractive focal point, i.e. the $0^{th}$ order. For asymmetric lenses e.g., making use of orders 0, +1, and +2, as in mentioned paper, apodization leads to an increasing energy distribution to far vision with increasing aperture. For a lens using a symmetric diffractive grating to provide far, near, and intermediate vision this simple method cannot be used for this purpose, since the refractive focal point in symmetric gratings is at or close to intermediate vision. Aforementioned WO2019130030A1 describes a way to improve the intensity distribution of sawtooth-based diffractive lenses using cross-apodization.

U.S. Pat. No. 8,486,141 B2 discloses a multi-zonal, monofocal ophthalmic lens comprising an inner zone, an intermediate zone, and an outer zone. The inner zone has a first optical power. The intermediate zone surrounds the inner zone and has a second optical power that is different from the first power by a magnitude that is less than at least about 0.75 Diopter. The outer zone surrounds the intermediate zone and has a third optical power different from the second optical power. In certain embodiments, the third optical power is equal to the first optical power. U.S. Pat. No. 9,968,440 B2 discloses an ophthalmic lens includes an optic having an anterior surface, a posterior surface, and an optical axis. At least one of the anterior surfaces and the posterior surface includes a first zone extending from the optical axis to a first radial boundary and a second zone extending from the first radial boundary to the edge of the optic. The first zone includes an inner region and an outer region separated by a phase shift feature, the phase shift comprising a ridge extending outwardly from the inner region and the outer region. U.S. Pat. No. 7,073,906B1 discloses a central aspherical monofocal zone that is arranged concentrically with a zone using an asymmetric diffractive grating.

For a lens to provide vision enough for a user to be spectacle independent it needs to provide far, intermediate, and near vision. In photopic conditions, when small pupils are present a full multifocal vision with an especially strong far vision is desired. But a central aperture of the lens that provides a very narrow far vision runs an increased risk of diopter mismatch. A central portion of the lens providing slightly stronger power than the intended power of far vision will decrease this risk. This is especially important since quality of the far vision is indeed what determines clinical success of cataract surgery. Additionally, such a distribution is also able to provide higher overall light efficiency when splitting the light with a diffraction grating, as will be shown below. Because of the well-known pinhole effect, causing a small pupil to provide a much higher depth of focus, small shifts in power for tiny pupils have no negative effect on vision. It is also important to be able to exactly choose the dominant power for very small apertures of a lens since different autorefractometry technologies might measure the post-operative power at different apertures and there might arise a need to change only the 1 mm dominant power to comply with a specific autorefractometry technology.

In mesopic conditions with slightly larger pupils the pinhole effect is no longer in effect making it very important for multifocal lens intended for spectacle independence to provide a strong near vision in addition to far vision. For full spectacle independence intermediate vision is also desired.

Due to the accommodation reflex human pupils constrict when viewing near objects, even in scotopic environments. Because of this, light focused for near vision at large pupils is physiologically not possible to use. Intermediate vision is much less afflicted by this problem, which on balance proves that reduction of light directed to near vision for large apertures is much more important than reduction of intermediate vision and that. Designing according to this principle ensures physiological efficiency of light in addition to technical light efficiency.

Accordingly, there is a need for an improved ophthalmic lens that utilizes the advantages of symmetric diffractive gratings, including very high light efficiency, in a way that allows for exact placement of the dominant optical power for tiny apertures, and a properly tuned energy distribution over a range of apertures to ensure also physiological efficiency of incident light.

OBJECTS OF THE PRESENT INVENTION

Primary object of the present invention is to provide an ophthalmic multifocal lens, comprising a refractive baseline, an optical axis and providing at least three focal points, one of them providing far vision to a user.

Another object of the present invention is to provide an ophthalmic multifocal lens comprising at least a first and a second portion, the portions being arranged concentrically around the optical axis, the first portion being the innermost.

A further object of the present invention is to provide an ophthalmic multifocal lens comprising a symmetric diffractive grating providing at least three focal points combined with the second portion, the $0^{th}$ order of said diffractive grating adds, to the optical power of said second portion, while the first portion, for a design wavelength, has a resulting dominant power that is between the intended powers of far and intermediate vision.

A still further object of the present invention is to provide an ophthalmic multifocal lens wherein said lens provides the ability to combine increased diffraction efficiency, with a much more anatomically correct use of the light lens using symmetric, sinusoidal diffractive gratings, the energy distribution being adapted properly for each aperture.

A still further object of the present invention is to provide an ophthalmic multifocal lens that allows for in-vivo measurements of the lens at a portion of the lens that has a different refractive power than the refractive baseline of the second portion with retained efficiency.

A still further object of the present invention is to provide an ophthalmic multifocal lens with optimized multifocality wherein the diffractive efficiency is greatly improved.

BRIEF DESCRIPTION OF THE PRESENT INVENTION

In a first aspect, there is provided an ophthalmic multifocal lens, at least comprising a focal point for far vision.

The lens having a light transmissive lens body comprising a symmetric (i.e. optical powers are symmetrically aligned around $0^{th}$ order) diffraction grating extending concentrically in a radial direction from an optical axis of the lens body across a part of a surface of the lens body. The lens comprises at least a refractive baseline and at least a first and a second portion, the portions being arranged concentrically around the optical axis, so that a concave shape in the center of the first portion is superpositioned onto the refractive baseline and provides an optical power that is between the intended power of far and intermediate vision, and in the second portion a symmetric diffractive grating superpositioned on to the refractive baseline, arranged so that, for a design wavelength, the $0^{th}$ order of the symmetric diffractive grating substantially coincides with the power of the refractive baseline as well as with an intended intermediate power of the lens.

The present disclosure is based on the insights that by carefully controlling the dominant power of the central area of a multifocal lens with a symmetric diffraction grating and further carefully control the exact shape and height of each ridge of said symmetric diffraction grating in a way so that the relative energy provided to near is higher for apertures of about 3 mm than for apertures of 2 mm as well as 4.5 mm and that the relative near energy for 5 mm and above is suppressed below that of intermediate energy, it is possible to make a lens that provides a very high diffraction efficiency as well as an higher physiological light efficiency.

As mentioned above, diffractive lenses having a continuous and smooth profile without any sharp edges are less susceptible to glare or scattering due to non-uniformities in the path that incident light travels through the lens, and also to produce less halos, while being easier to manufacture according to a calculated profile compared to sawtooth type or binary type gratings or reliefs, for example. A higher diffraction efficiency in any case leads to less stray light. For manufacturing technologies based on diamond turning or similar forms of machining a smooth profile will be more reliable as well as faster and cheaper to fabricate than profiles with sharp edges such as sawtooth or binary profiles.

An important step in the manufacturing of ophthalmic lenses by micro-machining or diamond turning, for example, is mechanical polishing to get rid of cutting traces. It is necessary to get rid of all visible cutting traces to comply with quality requirements and medical regulations for intraocular lenses. Obtaining extremely low levels of cutting traces, however, requires expensive machinery as well as slow cutting. If lenses are polished post-cutting, the machine may be allowed to work faster. Sharp angles, corners or edges in the height profile of diffractive lenses complicate the process of mechanical polishing. If mechanical polishing is not possible in view of the height profile of the lens, one needs to either utilize chemical polishing, which requires hazardous chemicals, or manufacture lenses without the requirement of polishing. The latter leads to much increased manufacturing costs because of one or both of lower yields and more expensive machinery.

Smooth diffractive geometries in accordance with the present disclosure allow for polishing and therefore lead to a significant increase in yield, compared to lenses having sharp transitions in their height profile.

BRIEF DESCRIPTION OF THE FIGURES OF
THE PRESENT INVENTION

Accompanying drawings are given solely for the purpose of exemplifying a multifocal aphakic diffractive multifocal lens, whose advantages over prior art were outlined above and will be explained in brief hereinafter.

The drawings are not meant to delimit the scope of protection as identified in the claims nor should they be referred to alone in an effort to interpret the scope identified in said claims without recourse to the technical disclosure in the description of the present invention.

FIG. 1 demonstrates a simplified anatomy of the human eye.

FIGS. 2a and 2b demonstrate a front and side view respectively of a typical ophthalmic multifocal aphakic intraocular lens as known in the art.

FIG. 3 demonstrates a schematic of the optical operation of a known periodic light transmissive circular disk-shaped lens body.

Figure 4A:
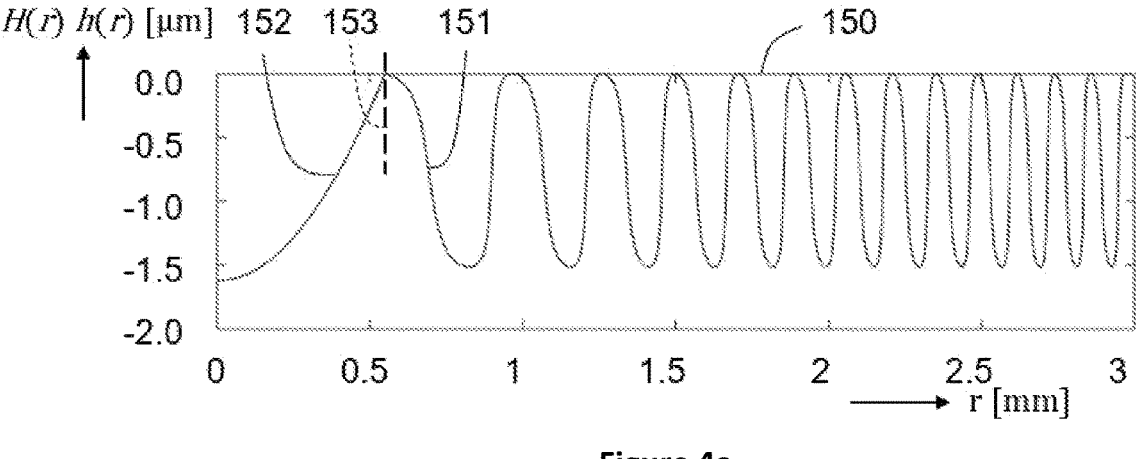
Figure 4B:
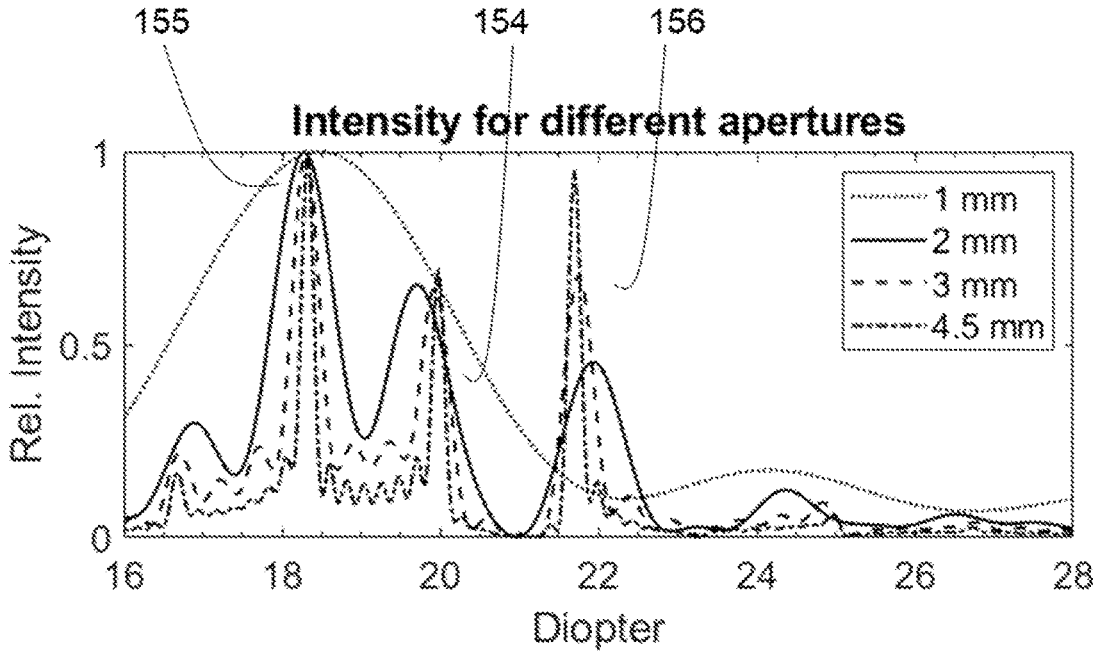

FIGS. 4a and 4b demonstrate a lens with a monofocal central zone with a symmetric multifocal grating as known in the art.

Figures 5A, 5B:
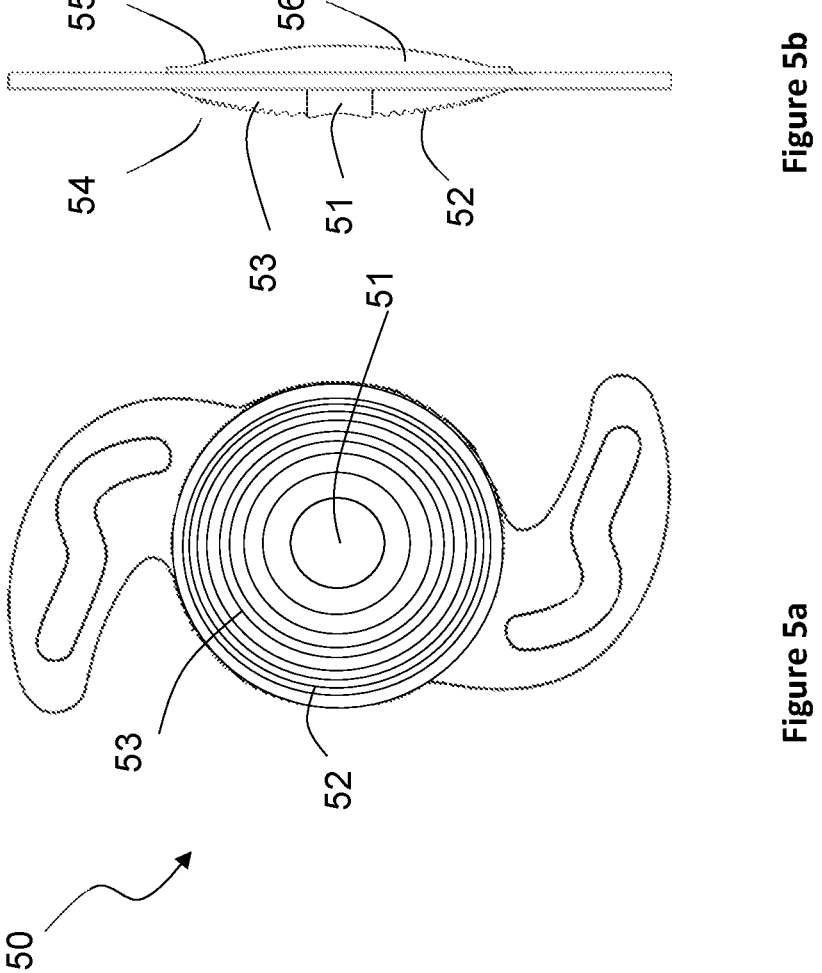

FIGS. 5a and 5b demonstrate a front and side view respectively of an ophthalmic multifocal aphakic intraocular lens according to one embodiment of the disclosed invention.

Figure 6A:
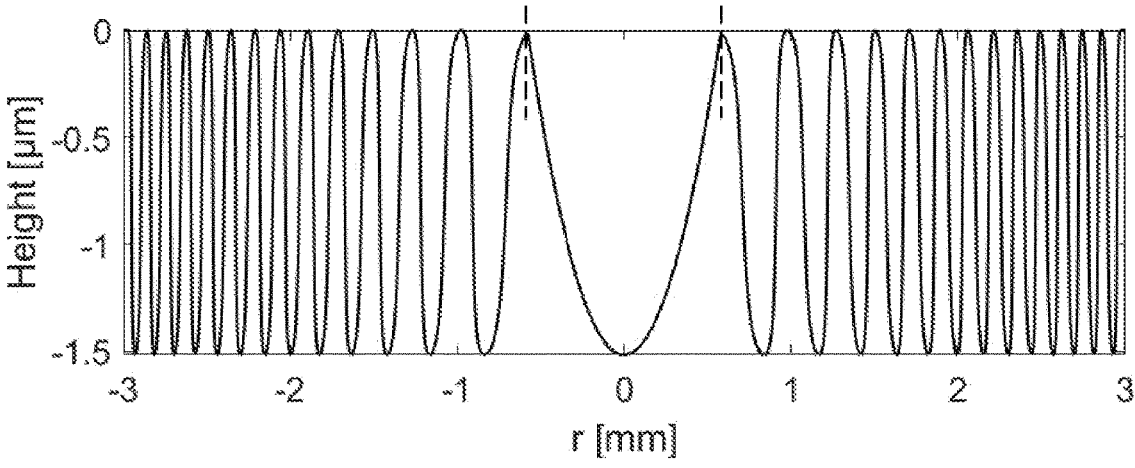
Figure 6B:
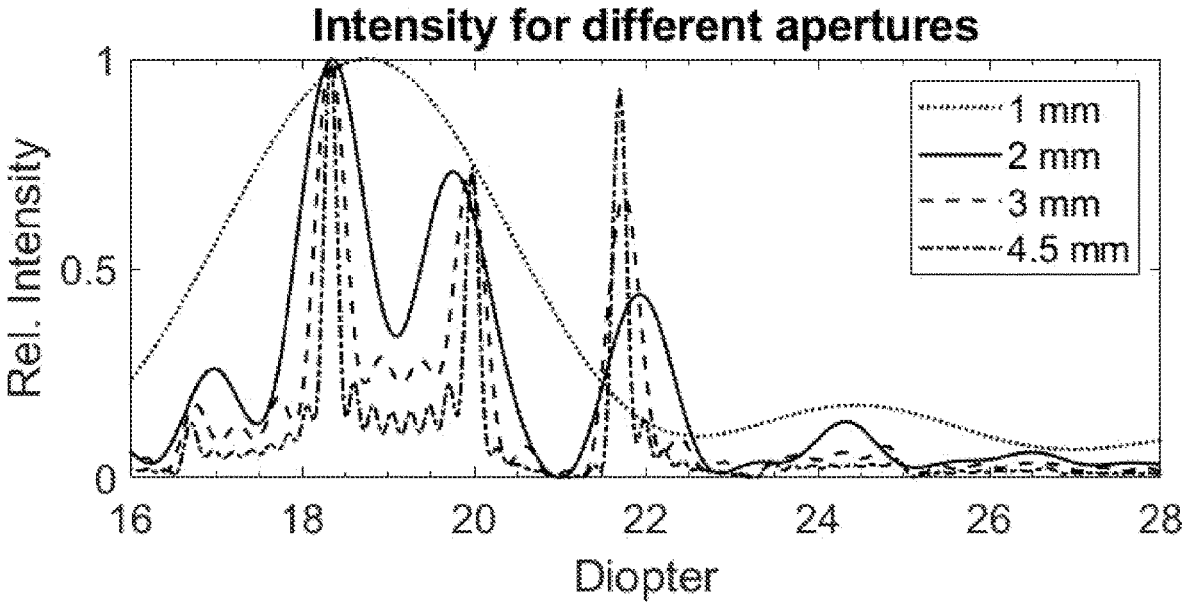

FIGS. 6a and 6b demonstrate a lens profile with a diffraction grating and a negative power central zone with adjusted power according to one embodiment of the disclosed invention.

Figure 7A:
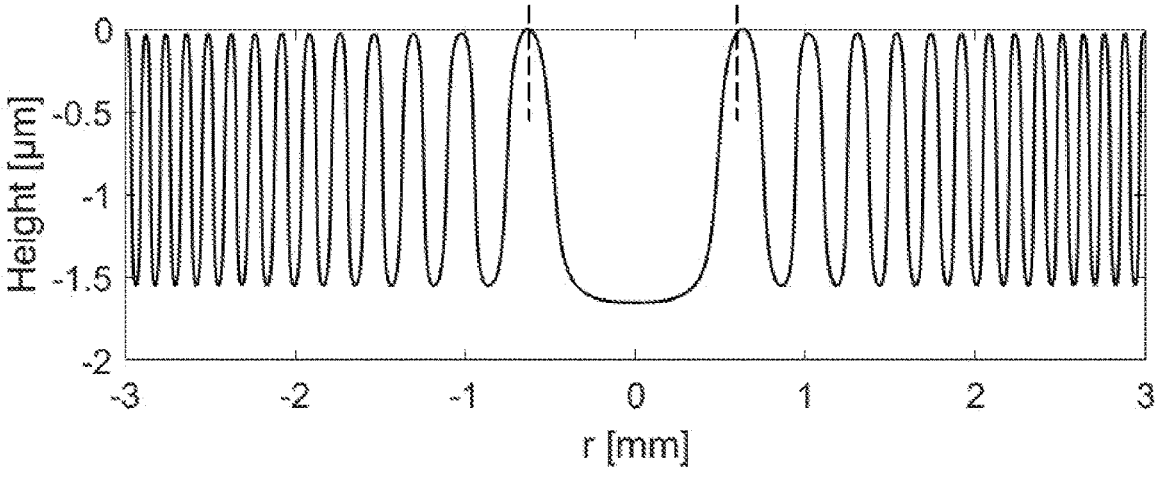
Figure 7B:
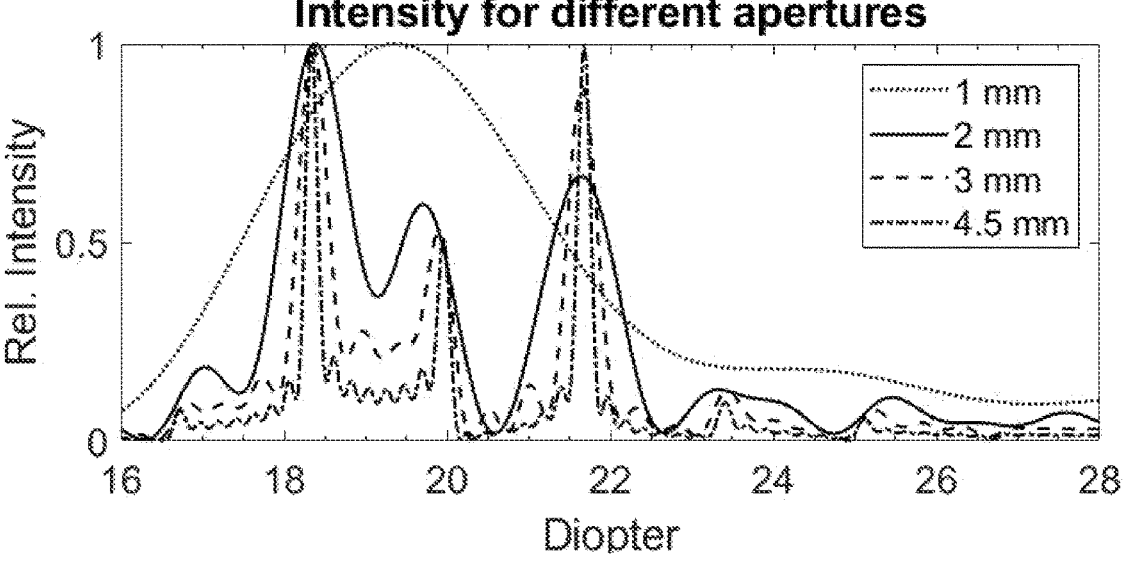
Figure 7C:
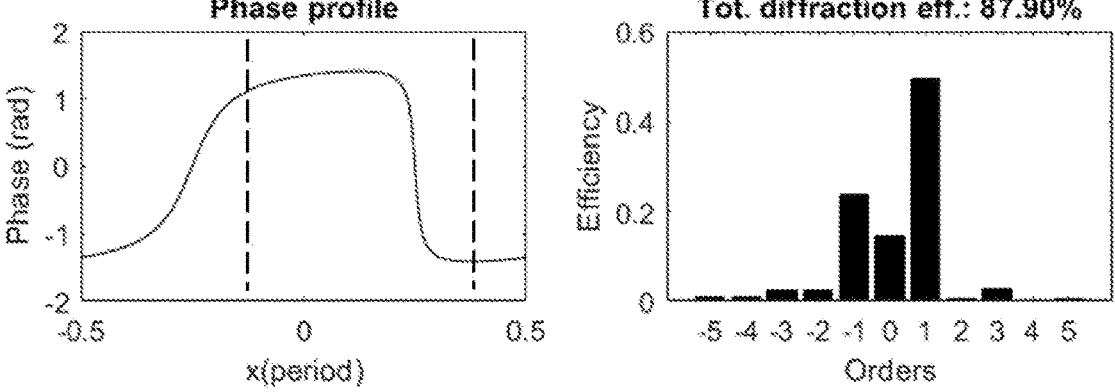

FIGS. 7a, 7b and 7c demonstrate a lens profile with a diffraction grating and a central zone with adjusted power according to one embodiment of the disclosed invention.

Figure 8:
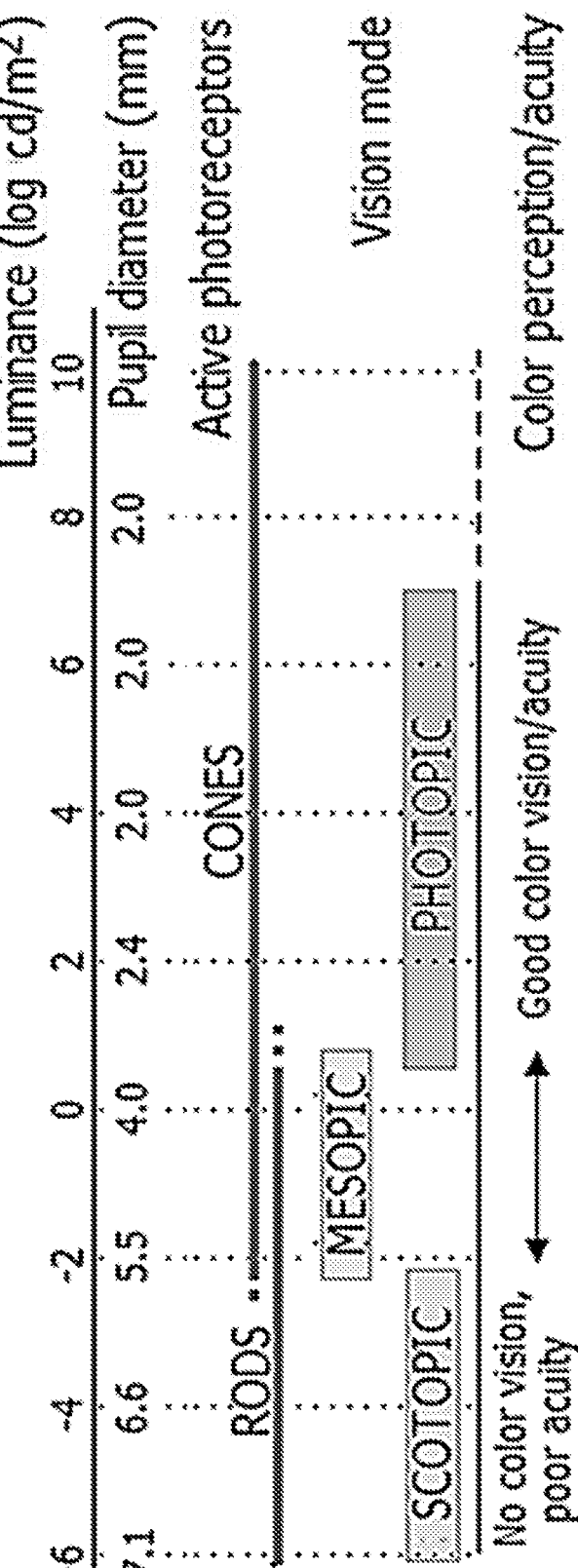

FIG. 8 demonstrates the respective activation properties of rods and cones in the eye.

Figure 9:
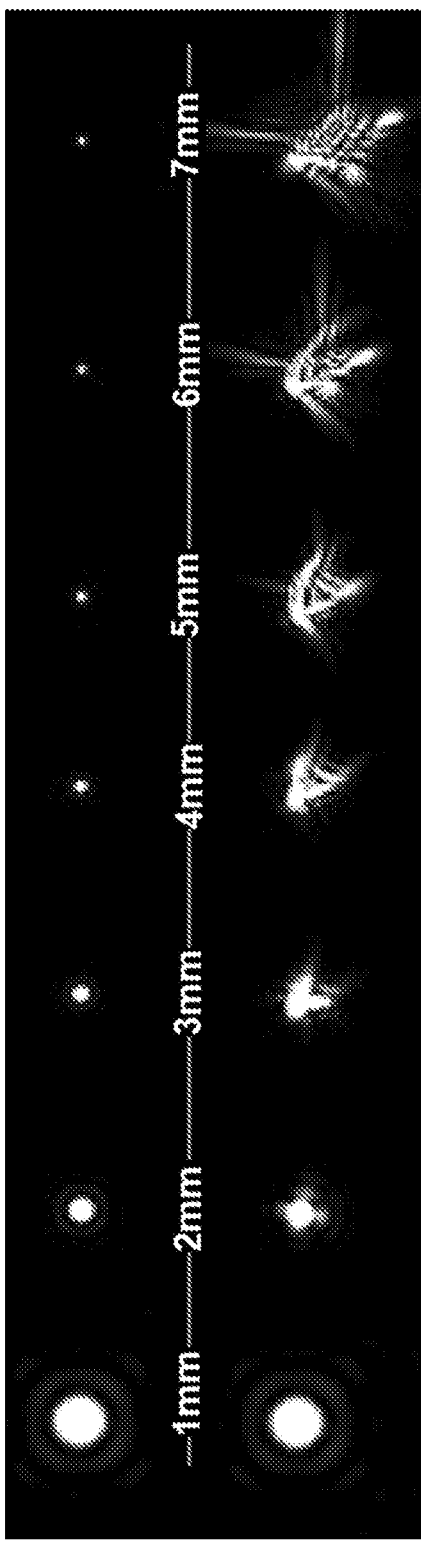

FIG. 9 demonstrates the point spread function (SPF) for different eyes and conditions.

Figure 10A:
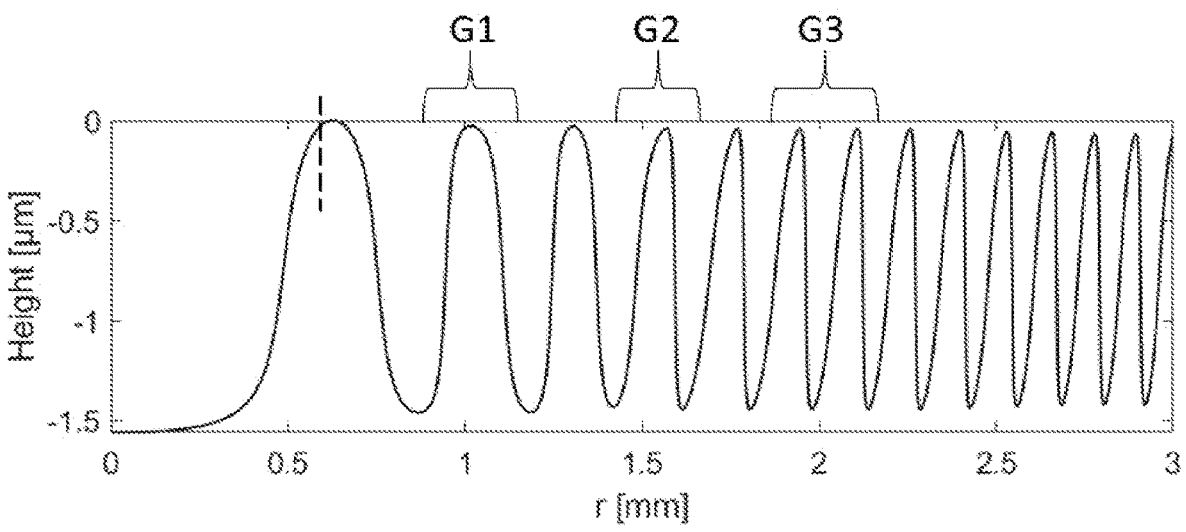
Figure 10B:
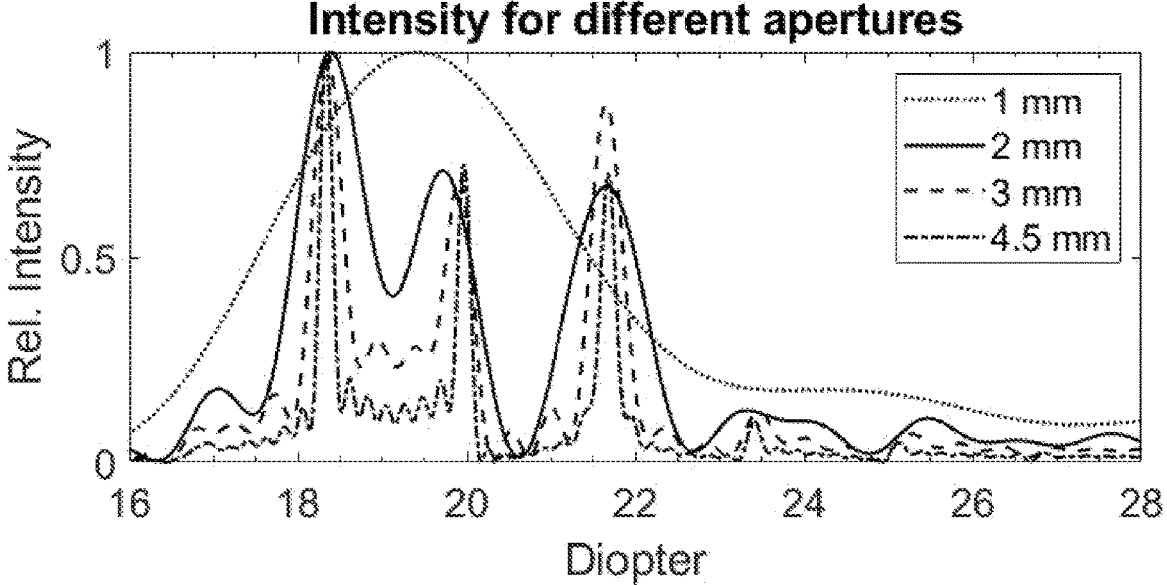

FIGS. 10a and 10b demonstrate a lens using a central zone that is substantially concave and promotes far vision very strongly according to one embodiment of the disclosed invention.

Figure 10C:
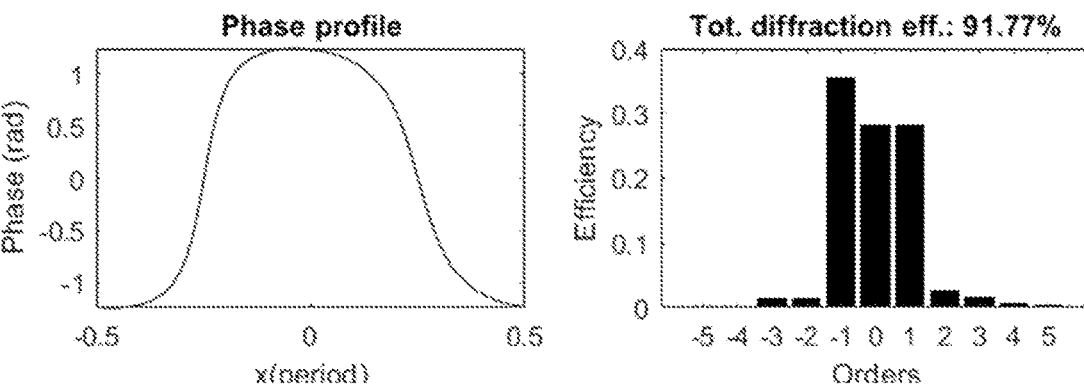
Figure 10D:
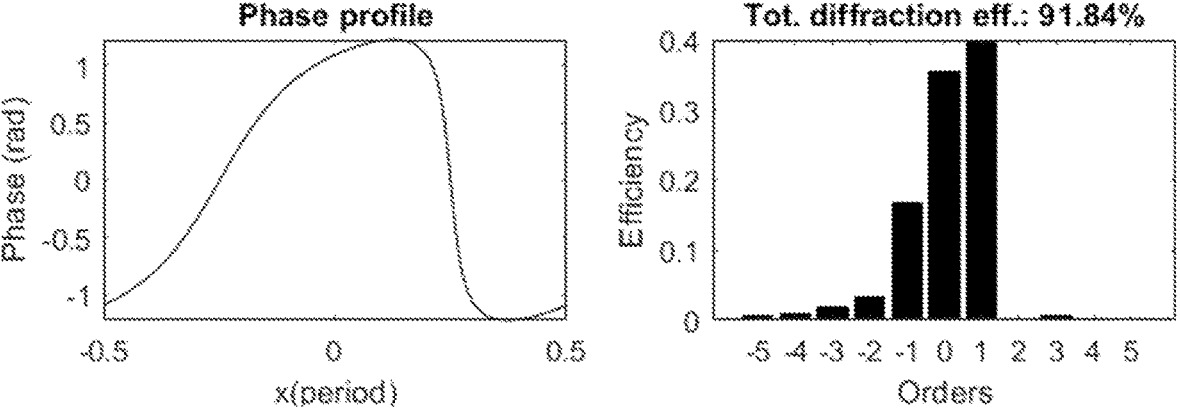
Figure 10E:
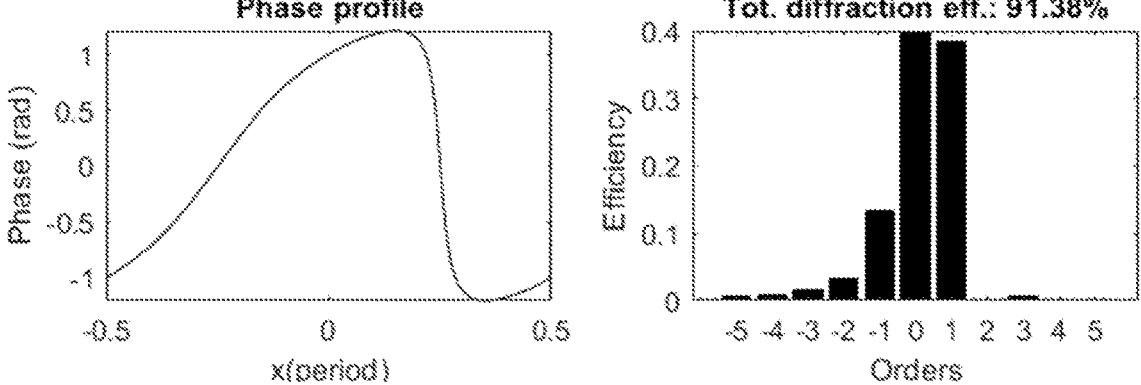

FIGS. 10c, 10d, and 10e demonstrate examples of underlying linear grating diffractive unit cells and their respective diffraction efficiencies according to one embodiment of the disclosed invention.

Figure 11A:
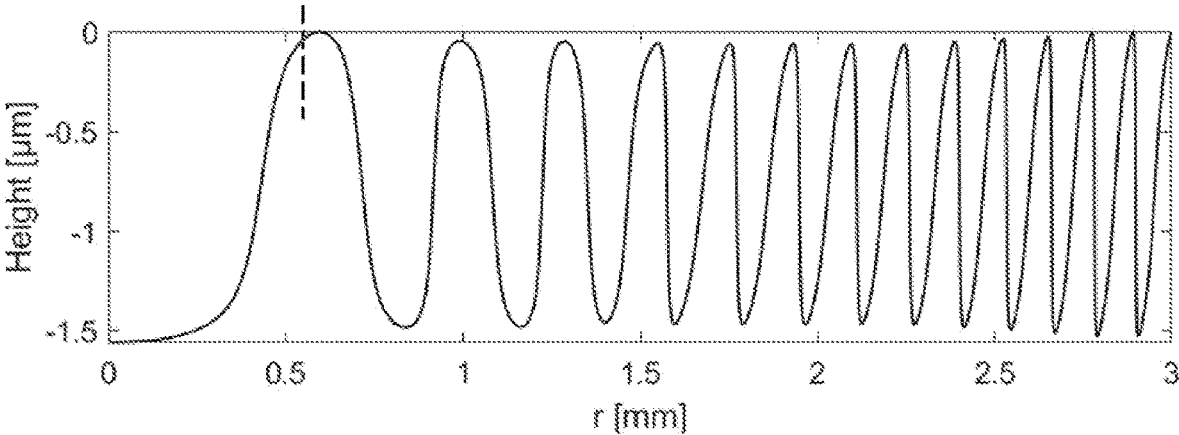
Figure 11B:
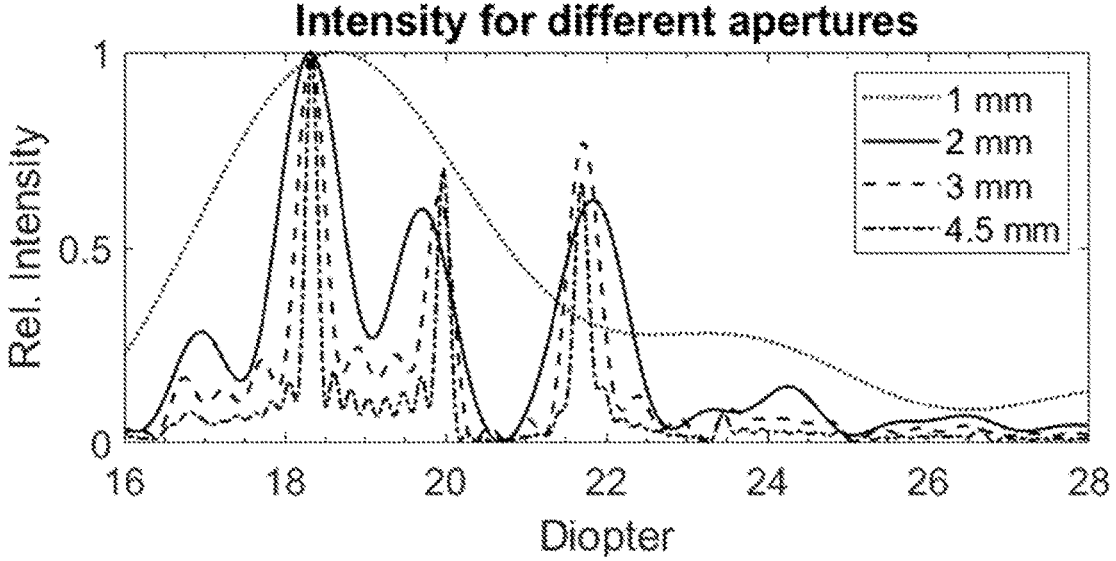

FIGS. 11a and 11b demonstrate a lens according to one embodiment of the disclosed invention.

Figure 12A:
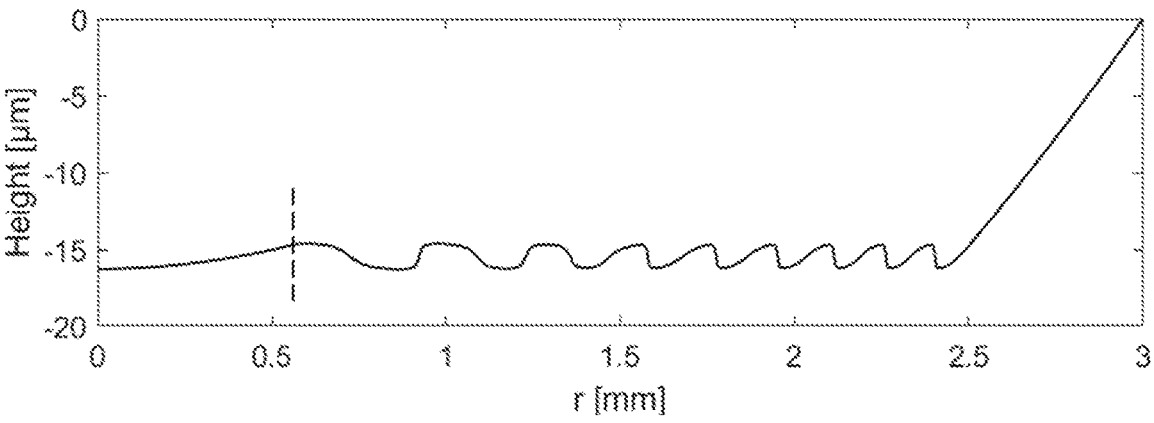
Figure 12B:
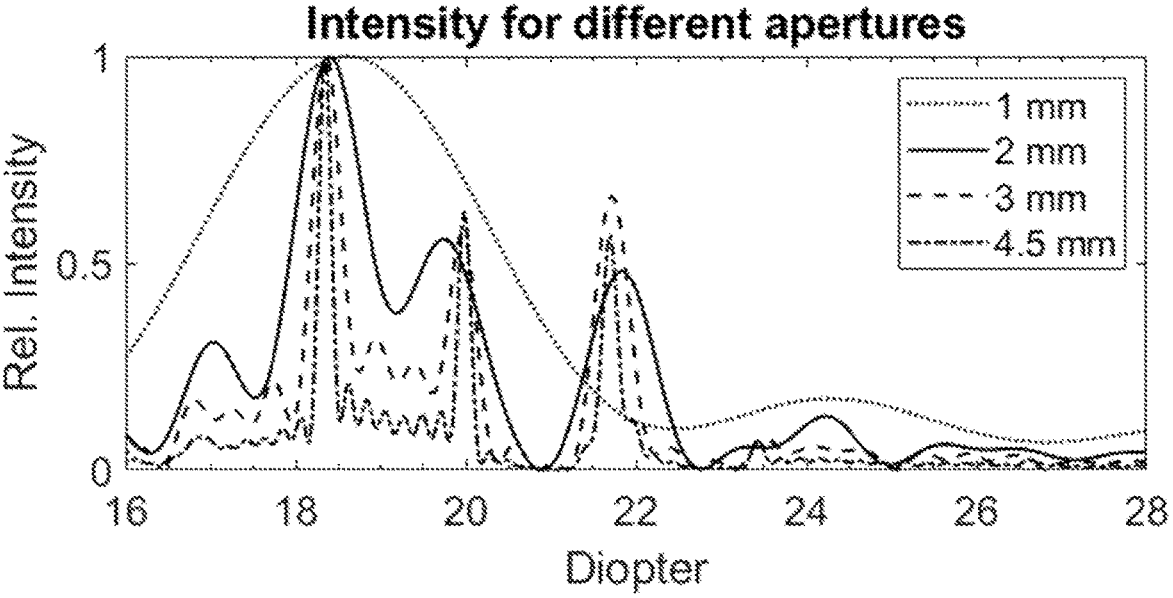

FIGS. 12a and 12b demonstrate a lens according to one embodiment of the disclosed invention.

Figure 13A:
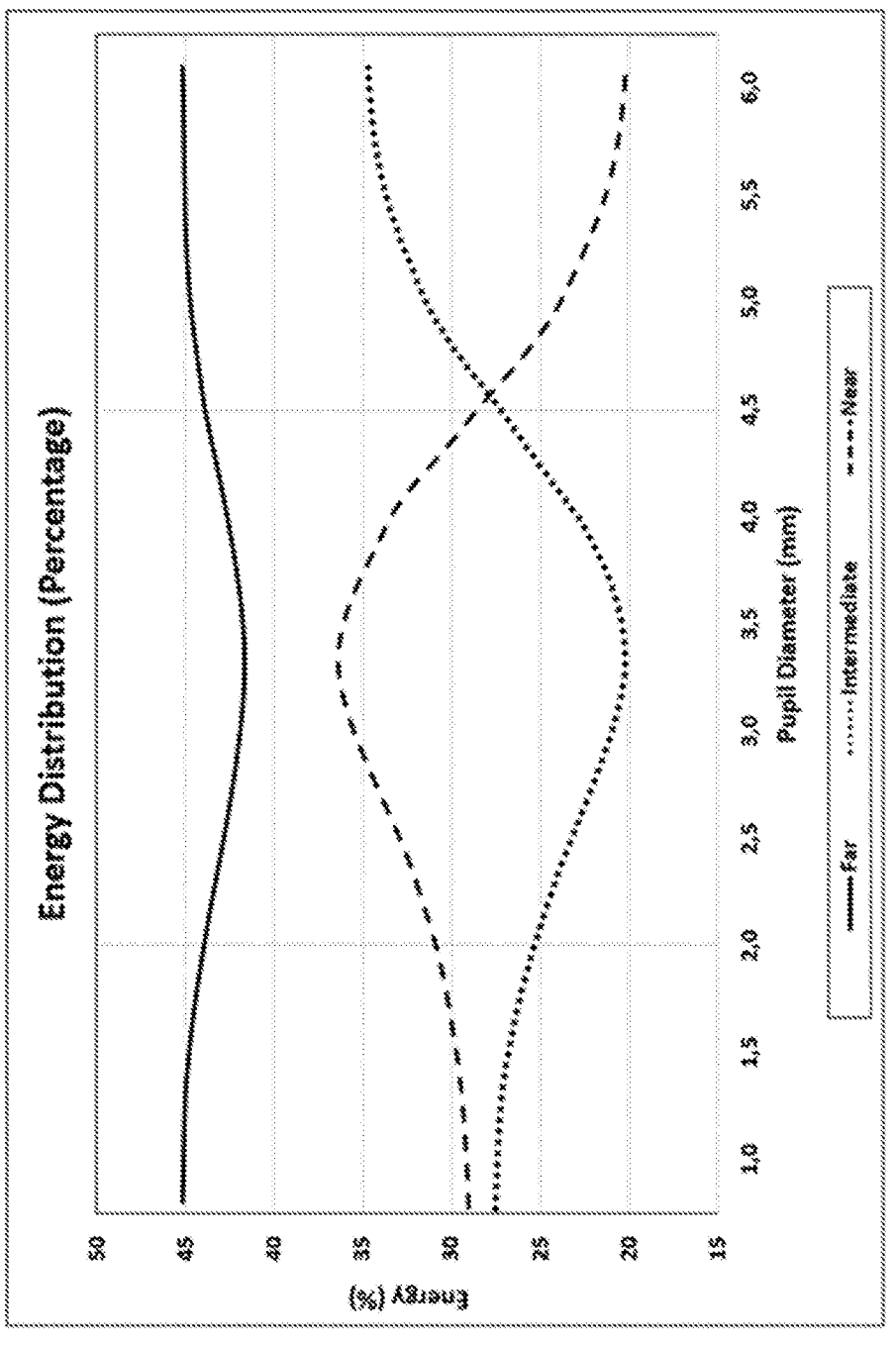

FIG. 13a demonstrates a possible design goal for energy distribution for a lens made according to one embodiment of the disclosed invention.

Figure 13B:
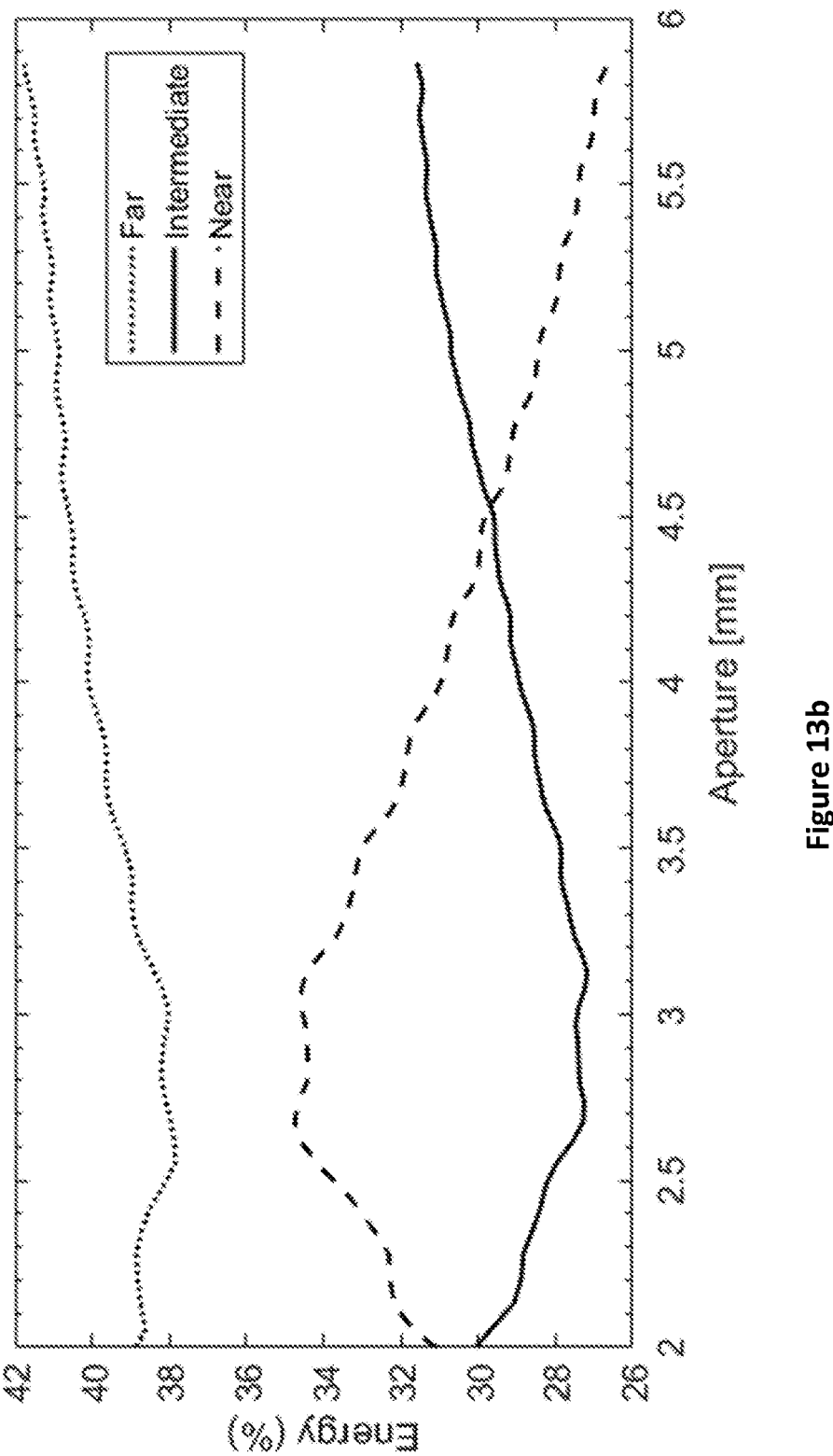

FIG. 13b demonstrates a simulated energy distribution of a lens made according to one embodiment of the disclosed invention.

DETAILED DESCRIPTION OF THE PRESENT
INVENTION

10 Eye
11 Cornea
12 Pupil
13 Natural crystalline lens
14 Retina
Posterior cavity
16 Anterior and posterior chambers
17 Far vision
18 Intermediate vision
19 Near vision
20 Optical axis
29 Optical axis 30 Ophthalmic lens
31 Lens body
32 Haptic(s)
33 Center part
34 Front surface
35 Rear surface
36 Diffraction grating
37 Optic diameter
38 Outer diameter
39 Center thickness
40 Lens
41 Lens body
42 Diffraction grating
43 DOE(s)
44 Light receiving surface
45 Center part
46 Primary light beam
47 Secondary light beam
48 Optical axis
50 Multifocal aphakic intraocular lens
51 Central lens portion
52 Symmetric multifocal grating
53 Peripheral lens portion
54 Anterior surface
55 Posterior surface
56 Lens body
150 Lens body surface
151 Symmetric multifocal diffraction grating
152 Monofocal central zone
153 Transition point
154 Intermediate vision focal point
155 Far vision focal point
156 Near vision focal point The vast majority of ophthalmic diffractive trifocal lenses make use of sawtooth profiles. Combining sawtooth profiles of two bifocal diffractive lenses to achieve trifocality is known in the art. This results in diffractive lenses with the usable orders arranged asymmetrically with respect to the $0^{th}$ order, e.g. a trifocal lens might make use of orders 0, +1, and +2 orders or 0, +2, and +3. Such diffraction gratings are henceforth referenced as asymmetric gratings.

One important property of diffractive gratings is the distinction between symmetric and asymmetric diffraction gratings. When ascribing symmetric or asymmetric property to multifocal ophthalmic lenses, what is considered is which orders it makes use of or renders useful. Symmetric diffractive lenses utilize of orders in a way that is symmetric around the $0^{th}$ order. Note that symmetric diffraction gratings are defined by which orders they utilize, not by the intensity of light distribution in these orders. Some symmetric diffractive lenses may be tuned so that there is a significant difference in light intensity between e.g. +1 and −1 orders, i.e. they have an unequal light distribution. A diffraction grating tuned as such would still be considered a symmetric diffraction grating. Most symmetric gratings discussed in this document will use an odd number of contiguous orders and the $0^{th}$ order, e.g. gratings used for trifocal lenses making use of order −1, 0, and +1 or gratings for pentafocal lenses making use of order −2, −1, 0, +1, and +2. However gratings not making use of the $0^{th}$ order can also be considered symmetric. Specifically the symmetric case of a grating making use of the four order −2, −1, +1, and +2 can in some cases be useful for ophthalmic lenses.

The highest possible diffraction efficiency for most useful intensity distribution for diffractive multifocal lenses with an odd number of foci, including trifocal lenses, is provided by smooth sinusoidal surfaces with usable orders symmetrically arranged around the $0^{th}$ order.

When comparing diffractive surfaces, an important factor is the diffractive efficiency. Diffraction efficiency is a measure of how much of the optical power is directed into the desired diffraction orders, or, when talking about diffractive lenses in particular, how much of the optical power is directed into the desired focal points. For bifocal lenses, where the surface of the lens body is optimized to provide an as good vision as possible at two distinct distances, the highest possible diffraction efficiency is reached by using the principles of a phase-matched Fresnel lens, which makes use of a sawtooth or jagged type diffraction pattern. Reference is made to the publication "Refractive and diffractive properties of planar micro-optical elements", by M. Rossi et al., in Applied Optics Vol. 34, No. 26 (1995) p. 5996-6007, which publication is herein incorporated by reference.

It is often advantageous to first consider linear phase grating since that field has a well-developed theory and can be utilized for diffractive lenses. For the special case of a trifocal linear grating with an equal intensity distribution to each order, it is shown specifically that the optimal solution is a structure without sharp edges in the publication "Analytical derivation of the optimum triplicator", by F. Gori et al., in Optics Communication 157 (1998), p. 13-16, which publication is herein incorporated by reference.

The publication "Theory of optimal beam splitting by phase gratings. I. One-dimensional gratings", by L. A. Romero and F. M. Dickey, in Journal of the Optical Society of America Vol. 24, No. 8 (2007) p. 2280-2295, which publication is herein incorporated by reference, discloses this more generally, proving that at the very least that optimal gratings for equal splitting into odd number of orders have continuous profiles. This latter paper provides the mathematical tools to find the optimal linear phase grating for any given set of target orders and any given intensity distribution among those target orders. The optimal grating is defined as the linear diffraction grating with the highest diffraction efficiency for the specified intensity distribution. It is noted that the publications by Gori et al. and Romero et al. discuss linear phase gratings only with the intent of creating beam splitters. By treating the x-axis of the linear grating as the $r^2$ space of a diffractive lens, any such linear phase can be turned into a lens. Using the theory from the study by Romero and Dickey it is possible to define the orders of interest and the relative intensity distributions of respective order and find the equation for the optimum (most efficient) grating for those input values. It further shows that at the very least symmetric gratings with a contiguous set of orders have optimum gratings without discontinuities for relatively equal intensity distributions. Some symmetric gratings with non-contiguous order sets also have gratings without discontinuities. In the Romero and Dickey study, only gratings with equal intensity distributions are shown, however using the provided theory gratings with non-equal distributions are also documented. It should be noted that this is one specific way to optimize linear phase gratings. Additionally, there are effects specific for lenses not taken into account by optimization of linear phase gratings, optimizing for these effects can be advantageous when designing lenses according to the present invention.

One important part of the design of a lens according to the present invention is to find a set of symmetric diffractive unit cells without discontinuities that can be used together to provide the desired intensity distribution. There are different ways to calculate and tune symmetric diffractive lenses in the art. One way is to use optimized linear grating transformed into diffractive lenses, as described above and in further detail PCT/EP2019/080758. One early example of a lens based on a symmetric diffractive grating is the 7-focal lens described in the paper by Golub et al., "Computer generated diffractive multi-focal lens" published in Journal of modern optics 39, no. 6 (1992): 1245-1251. As a continuation of this, additional embodiments in the already mentioned Osipov 2015 study as well as the study published in 2012 by Osipov et al. called "Fabrication of three-focal diffractive lenses by two-photon polymerization technique" published in Applied Physics A 107, no. 3 (2012): 525-529. In these papers trifocal, symmetric lenses made by modifications to a sinus grating are disclosed. In these studies by Osipov et al. only one unit cell is used per lens, but with what we now know the diffractive grating for an properly adaptive lens could be constructed from a set of modified sinus gratings made as described. A different approach is also disclosed in U.S. Pat. No. 5,760,871A and IL104316, where a so called asymmetric super Gaussian formula is used to design trifocal gratings with unequal intensity distribution. A set of such diffraction unit cells could be used together, with proper transition zones, to form a proper diffraction grating for an adaptive lens according to the patent. Yet another method is the one described in WO2020053864A1, where the Gerchberg-Saxton iterative algorithm is used to design the surface profile of a pentafocal (having five focal points) lens with a symmetric diffraction grating.

The lens according to the present invention is an ophthalmic lens comprising at least a refractive baseline and at least a first and a second portion, the portions being arranged concentrically around the optical axis, so that a concave shape in the center of the first portion is super positioned onto the refractive baseline and provides an optical power that is between the intended power of far and intermediate vision, and in the second portion a symmetric diffractive grating super positioned on to the refractive baseline, arranged so that, for a design wavelength, the $0^{th}$ order of the symmetric diffractive grating substantially coincides with the power of the refractive baseline as well as an intended intermediate power of the lens.

Proposed multifocal ophthalmic lens addresses problems known in the art as follows: Insofar as symmetrical multifocal diffraction gratings are applied, several problems tend to present themselves such as the combination of a monofocal central zone (providing only far vision) and a multifocal grating with fixed diffraction efficiencies optimized for an aperture of 3 mm, as known in the art, leading to an imbalanced lens, wherein the near vision is particularly overly strong for large apertures. Another one of such technical difficulties to be solved is when a strictly monofocal central zone with optical power exactly coinciding with the diffractive focal point responsible for far vision leads to a decrease in overall efficiency.

Above mentioned difficulties notwithstanding, a strong far vision is the typical criterion to ascertain the success of cataract surgery. This is because a strong far vision is important for all apertures.

As such, disclosed invention specifically concerns the creation of an adaptive multifocal lens comprising a symmetric multifocal diffraction grating. Adaptivity is here defined as a measure of functional light utilization for the human eye. The eye has a much larger depth of field at pupil sizes that are smaller, due to the pinhole effect. Pupil size, not being solely dependent on the pupillary light reflex, is also dependent on the accommodation reflex, which causes the pupil not sufficiently enlarging while focusing on objects of closer proximity. Disclosed invention also addresses this problem so that the power of the central portion of said multifocal lens is adjusted to increase the efficiency and therefore success rate of cataract surgery whilst maintaining the inner 1-mm aperture to essentially provide far vision. This is detailed hereinafter.

According to the study by Kanellopoulos and Asimellis titled "Clear-cornea cataract surgery: pupil size and shape changes, along with anterior chamber volume and depth changes. A Scheimpflug imaging study." *Clinical Ophthalmology* (Auckland, NZ) 8 (2014): 2141, cataract surgery on average decreases the photopic pupil with 0.27 mm. Additionally, the pupil sizes reported in medical literature is often the apparent pupil, since it can be measured by optical inspection. However, the more relevant pupil is the anatomical pupil, located closer to the natural lens (in the phakic eye). Following from the Kanellopoulos-Asimellis study, the apparent pupil can be considered as the entrance pupil of the optical system of the eye, while the anatomical pupil is the aperture stop. According to the model in mentioned study, the apparent pupil is 13.1% larger than the anatomical pupil. This will of course vary between individuals as well as between environmental conditions. The apertures referred to in this document are the physical apertures of the eye, specifically of the aphakic and pseudophakic eye. In the medical literature naturally occurring pupil sizes are often given as 2 mm to 8 mm, but for IOLs the relevant aperture size is in most cases up to 5 mm diameter and 6 mm at the most.

In addition to the pupillary light reflex the pupil also responds to the accommodation reflex. The accommodation reflex is a response to focusing on a nearby object and one of its effects is that of constricting the pupil. Because of this latter effect even in scotopic conditions the pupil will not be very large while focusing on nearby objects. Because of this additional near vision provided by an intraocular lens for large pupils is mostly wasted and is ideally not provided.

For small pupil sizes the pinhole effect is important to consider. A constriction of the pupil increases the depth of focus of the lens, for tiny pupils this effect generally provides a relatively good vision at all distances even with a lens that is providing only a single focus. Many modern multifocal- and enhanced depth-of-focus (EDOF) lenses takes advantage of this effect by allowing the light provided by the lens to be dominated by intermediate or near vision. The argument is that if this is provided in the center of the lens it will work well enough for the user in photopic conditions, because of large depth of field for tiny apertures, while this intensity provided for near and/or intermediate vision can be of use especially for mesopic conditions with slightly larger pupil sizes. A non-diffractive example of higher power in the central region with decreasing power for increasing radius is disclosed in U.S. Pat. No. 10,028,825 with so called continuous power progressive intraocular lenses that introduces a changing power without the use of abrupt steps. While that can be acceptable it is not the ideal solution, as an excellent far vision is seen as the most important parameter of IOLs and the quality of the far vision is indeed what determines clinical success of cataract surgery. Because of this it is important for an IOL to provide a strong far vision for all apertures, with the possible exception for very tiny pupils. Additionally, ophthalmologists often expect the autorefractometer to measure the far in the post-operative eye, and a central power that is too much removed from the far power of the lens can lead to confusion in evaluation of the cataract surgery success. However, a small shift of power towards stronger diopters for very small apertures can be of use to increase the so-called landing zone or sweet spot to increase the chance of clinical success, but in the ideal case this shift should not be as large as to go all the way to an intermediate addition (approximately between 1.5 D to 2.2 D) and certainly not to a near addition (approximately between 3 D and 4.4 D). An ideal shift in the central 1 mm aperture should be below 1.2 D and, in any case, the dominant focus at 1 mm should be below that of the intended intermediate power. It should be noted here that at 1 mm aperture there is usually no developed multifocality. The measured intensity- or MTF-curve will have one dominant peak.

On the other hand, the addition of near and intermediate powers is important for mesopic conditions to enable viable vision for most ranges. Usually, it is desirable to keep the near vision stronger than the intermediate vision to provide a good reading capability without the use of glasses.

It can then be summarized that what is desired is a multifocal lens where the multifocality is provided by a multifocal symmetric grating and for tiny pupils (e.g. 1 mm) the dominating focus should be corresponding to far vision with a slightly stronger optical power than the intended far power, or at the very least weaker than the intended power of the intermediate vision. At 2 a mm aperture a well-developed multifocality (at least three foci) should be present. For pupil sizes of around 3 mm the ideal diffractive multifocal lens should provide strong far vision, strong near vision, and some intermediate vision. For pupils larger than 4.5 mm energy directed to near vision cannot not be used well by the eye. Because of this additional energy directed to near vision should be minimized or small and the energy going to near for 4.5 mm pupil should be less than that for both intermediate and near.

FIG. 1 shows, in a simplified manner, the anatomy of the human eye 10, for the purpose of illustrating the present disclosure. The front part of the eye 10 is formed by the cornea 11, a spherical clear tissue that covers the pupil 12. The pupil 12 is the adaptable light receiving part of the eye 10 that controls the amount of light received in the eye 10. Light rays passing the pupil 12 are received at the natural crystalline lens 13, a small clear and flexible disk inside the eye 10, that focuses light rays onto the retina 14 at the rear part of the eye 10. The retina 14 serves the image forming by the eye 10. The posterior cavity 15, i.e. the space between the retina 14 and the lens 13, is filled with vitreous humour, a clear, jelly-like substance. The anterior and posterior chambers 16, i.e. the space between the lens 13 and the cornea 11, is filled with aqueous humour, a clear, watery liquid. Reference numeral 20 indicates the optical axis of the eye 10.

For a sharp and clear far field view by the eye 10, the lens 13 should be relatively flat, while for a sharp and clear near field view the lens 13 should be relatively curved. The curvature of the lens 13 is controlled by the ciliary muscles (not shown) that are in turn controlled from the human brain. A healthy eye 10 is able to accommodate, i.e. to control the lens 13, in a manner for providing a clear and sharp view of images at any distance in front of the cornea 11, between far field and near field.

Ophthalmic or artificial lenses are applied to correct vision by the eye 10 in combination with the lens 13, in which cases the ophthalmic lens is positioned in front of the cornea 11, or to replace the lens 13. In the latter case also indicated as aphakic ophthalmic lenses.

Multifocal ophthalmic lenses are used to enhance or correct vision by the eye 10 for various distances. In the case of trifocal ophthalmic lenses, for example, the ophthalmic lens is arranged for sharp and clear vision at three more or less discrete distances or focal points, often including far intermediate, and near vision, in FIG. 1 indicated by reference numerals 17, 18 and 19, respectively. Far vision is in optical terms when the incoming light rays are parallel or close to parallel. Light rays emanating from objects arranged at or near these distances or focal points 17, 18 and 19 are correctly focused at the retina 14, i.e. such that clear and sharp images of these objects are projected. The focal points 17, 18 and 19, in practice, may correspond to focal distances ranging from a few meters, to tens of centimeters, to centimeters, respectively. Usually, ophthalmologists choose lenses for the patients so that the far focus allows the patient to focus on parallel light, in the common optical terminology it is that the far is focused on infinity. Ophthalmologists will, when testing patients, commonly measure near vision as 40 cm distance from the eyes and intermediate vision at a distance of 66 cm, but other values can be used.

The amount of correction that an ophthalmic lens provides is called the optical power, OP, and is expressed in Diopter, D. The optical power OP is calculated as the inverse of a focal distance f measured in meters. That is, OP=1/f, wherein f is a respective focal distance from the lens to a respective focal point for far 17, intermediate 18 or near vision 19. The optical power of a cascade of lenses is found by adding the optical powers of the constituting lenses, for example. The optical power of a healthy human lens 13 is about 20 D.

FIG. 2a shows a top view of a typical ophthalmic multifocal aphakic intraocular lens 30, and FIG. 2b shows a side view of the lens 30. The lens 30 comprises a light transmissive circular disk-shaped lens body 31 and a pair of haptics 32, that extend outwardly from the lens body 31, for supporting the lens 30 in the human eye. Note that this is one example of a haptic, and there are many known haptic designs. The lens body 31 has a biconvex shape, comprising a center part 33, a front or anterior surface 34 and a rear or posterior surface 35. The lens body 31 further comprises an optical axis 29 extending transverse to front and rear surfaces 34, 35 and through the center of the center part 33. Those skilled in the art will appreciate that the optical axis 29 is a virtual axis, for the purpose of referring the optical properties of the lens 30. The convex lens body 31, in a practical embodiment, provides a refractive optical power of about 20 D.

In the embodiment shown, at the front surface 34 of the lens body 31 a periodic light transmissive diffraction grating or relief 36 is arranged, comprised of rings or zones extending concentrically with respect to the optical axis 29 through the center part 33 over at least part of the front surface 34 of the lens body 31. The diffraction grating or relief 36 provides a set of diffractive focal points. Although not shown, the diffraction grating or relief 36 may also be arranged at the rear surface 35 of the lens body 31, or at both surfaces 34, 35. In practice, the diffraction grating 36 is not limited to concentric circular or annular ring-shaped zones, but includes concentric elliptic or oval shaped zones, for example, or more in general any type of concentric rotational zone shapes.

In practice the optic diameter 37 of the lens body 31 is about 5-7 mm, while the total outer diameter 38 of the lens 30 including the haptics 31 is about 12-14 mm. The lens 30 may have a center thickness 39 of about 1 mm. In the case of ophthalmic multifocal contact lenses and spectacle or eye glass lenses, the haptics 32 at the lens body 31 are not provided, while the lens body 31 may have a plano-convex, a biconcave or plano-concave shape, or combinations of convex and concave shapes. The lens body may comprise any of Hydrophobic Acrylic, Hydrophilic Acrylic, Silicone materials, or any other suitable light transmissive material for use in the human eye in case of an aphakic ophthalmic lens.

FIG. 3 schematically illustrates, the optical operation of a known periodic light transmissive diffraction grating or relief 42 of a lens 40 comprising a biconvex light transmissive circular disk-shaped lens body 41. This type of lens, combining refractive and diffractive power is also referred to as a hybrid lens. The lens 40 is shown in a cross-sectional view in radial direction of the lens body. The diffraction grating or relief 42 comprises a plurality of repetitive, contiguously arranged, prism shaped transparent diffractive optical elements, DOEs, 43. The DOEs 43 extend in concentric zones around the center part 45 of the lens body 41, in a manner similar to the rings or zones of the grating or relief 36 shown in FIG. 2a. For illustrative purposes, the DOEs 43 of the diffraction grating 42 are shown as well-known jagged or saw-tooth type elements, comprising a continuous, sloping light receiving surface 44, such as a linear or curved sloping light receiving surface 44. Gratings or reliefs in which the DOEs 43 alternate between two heights, spaced apart in radial direction of the lens body 41, are called binary type reliefs (not shown). The repetition period or pitch of the DOEs 43 monotonically decreases in radial direction from the center or optical axis of the lens and varies with the square of the radial distance.

Pitch depends on the refractive index, the design wavelength, and the optical power of the first diffraction order. Pitch is determined so that the optical path difference (OPD) through the lens to the focal point of the first order has a difference of exactly one wavelength per period. To visualise the periodicity of a diffraction grating, one would often plot the diffractive lens profile versus the square of the radius. When plotted as such, the periods (grating pitch) are equidistant, more exactly the period pitch in $r^2$ is $|2\lambda f|$, where $\lambda$ is the design wavelength and f the inverse of the optical power of the first diffractive order.

In the art, one side of the lens is purely refractive, while the other side has a diffractive grating superpositioned over a refractive base line. The refractive baseline can be e.g., spherical or having some sort of aspherical shape. The diffractive pattern, which is added onto the refractive baseline, may in general be applied to any of the two sides of the lens. Therefore, if a diffractive pattern is to be combined with a refractive surface with some special feature, it generally bears little importance if they are added to the same side or, if one is added to a first side and the other to a second side of the lens. Concurrently, two diffractive patterns may be combined either by super positioning on one side, or by adding them in an overlapping fashion on separate sides. In the disclosures pertaining to the present invention, combining of two lens structures shall always be understood as allowing for both possibilities. The optical power of the lens for a specific diffraction order are calculable by addition of the refractive base power and the optical power of that diffractive order.

An incident or primary light beam 46 that passes the grating 42 and the lens body 41 is, respectively, diffracted and refracted and results in an output or secondary light beam 47. The refracted and diffracted light waves i.e. secondary light beams 47 form a plurality of focal points at the optical axis 48 of the lens 40, due to constructive interference of the light waves 47. Constructive interference occurs when the optical path difference between light waves 47 arriving from the lens body 41, at a particular focal point, is an integer multiple of their wavelength, i.e. the light waves are in-phase, such that their amplitudes add-up in a reinforcing manner. When the difference in optical path length travelled by interfering light waves 47 from the lens body 41 is an odd multiple of half of the wavelength, such that a crest of one wave meets a trough of another wave, the light waves 47 partly or completely extinguish each other, i.e. the light waves are out of phase, not resulting in focal points at the optical axis 48 of the lens body 41.

The points of constructive interference at various distances from the lens body 41 are generally designated diffraction orders. The focal point that corresponds to the focal point that originates due to refractive operation of the curvature of the lens 40 is indicated by order zero, 0. The other focal points are designated by orders +m and −m, wherein m is a positive integer value. That is, m=+1, +2, +3, etc. if the respective focal point occurs at the left-hand side of the zero order when viewed in the plane of the drawing, i.e. at a distance in the direction towards the lens body 41, and designated by orders m=−1, −2, −3, etc. if the respective focal point occurs at the right-hand side of the zero order when viewed in the plane of the drawing, i.e. at a distance in the direction away from the lens body 41. Such as illustrated in FIG. 3.

It is noted that the above allocation of the positive and negative diffraction orders in some publications and handbooks may be reversed with respect to their position relative to the zero order. This, for example, becomes the case when the theory in the publication by Romero et al is applied directly as has been done here. If not otherwise indicated, the present description adheres to the convention as shown in FIG. 3.

The diffraction relief 42 can be designed to provide focal points at different distances from the lens body 41. The periodic spacing or pitch of the DOEs 43 substantially determines where the points of destructive and constructive interference occur at the optical axis 48 of the lens, i.e. the position of the diffractive orders at the optical axis 48. By the shape and height of the DOEs 43 the amount of incident light that is provided at a point of constructive interference, i.e. at or in a particular diffraction order, is controlled.

In case of a diffraction grating or relief 42 providing diffraction orders that are regularly spaced at both sides of the zero order, the grating or relief is called a symmetric wave splitter or diffractive grating, as the incident light beam 46 is diffracted or split into orders that are symmetrically arranged with respect to the zero order. A grating or relief producing a non-regular spacing of diffractive orders, such as +1, +2, −3, −5 is called an asymmetric diffractive grating. The common cases of diffraction gratings producing usable orders at 0th order and +1 or $0^{th}$, +1, and +2 are also asymmetric diffractive gratings.

The light energy in light waves (secondary light beams 47) that are focused or diffracted in focal points or orders that do not contribute to image forming at the retina 14 of the human eye 10 is lost and reduces the overall efficiency of the lens 40, and hence the quality of images perceived by a human being using such lens. In practice, for optimally designing a lens, it is advantageous if the focal points for providing or correcting far, intermediate and near vision to the human eye, such as illustrated in FIG. 1, for example, can be set beforehand, and a diffraction grating 42 is provided that maximizes the overall efficiency of the light energy received from the incident light beam 46 in these pre-set focal points is optimal.

In scientific literature, a diffraction grating optimizing overall efficiency of the light distribution in pre-set or target diffraction orders is found from determining a linear phase-only function or phase profile that generates the target diffraction orders with a maximum overall efficiency n or figure of merit defined as the sum of the normalized light energies of all these target orders. These diffractive gratings can then be shaped into lenses by adjusting the argument so that they have equidistant periods in the $r^2$ space.

Those skilled in the art will appreciate that the lens body 41 may comprise a plano-convex, a biconcave or plano-concave shape, and combinations of convex and concave shapes or curvatures (not shown).

FIGS. 4a and 4b illustrate a lens and the functionality of said lens according to PCT/EP2019/080758 by combining a monofocal central zone with a symmetric multifocal grating. FIG. 4a illustrates, by way of example, a height profile or amplitude profile of another embodiment of a trifocal ophthalmic lens in accordance with the present disclosure, along a linear scale as function of the radial distance r, expressed in mm. The amplitude profile or height profile of the embodiment of the ophthalmic lens illustrated in FIG. 15a comprises the surface of the lens body 150, in turn comprising a monofocal central zone, indicated by reference numeral 152 and a diffraction grating 151. The optical axis, running through the center of the lens body, is assumed to be at a radial position r=0, whereas the radial distance r measured in outward direction from the optical axis is expressed in mm along the vertical axis. Reference numeral 160 refers to the outer circumference of the front surface 34 of the lens body 30, as illustrated in FIGS. 2a and 2b. The central zone 152 is monofocal and arranged in this example to have a power coinciding with one for the focal points of the diffraction grating 151.

At a transition point 153, at a radial position of the lens body at a distance of about 0.5 mm from the optical axis, the continuous amplitude profile h(r) 152 of the monofocal central zone ends and continuous in the symmetric multifocal diffraction grating profile H(r) 151 of the diffraction grating. In the embodiment shown, the transition point 153 is at the surface 150 of the lens body.

In this example, the design wavelength λ of the lens is assumed at 550 nm, the index of refraction n of the lens body is set to 1.492, and the index of refraction n_m of the medium surrounding the lens body is assumed 1.336.

FIG. 4b shows the intensity simulation of the lens in FIG. 4a for four different aperture sizes, 1 mm, 2 mm, 3 mm, and 4.5 mm. The aperture, or the pupil, is assumed to correspond to double radius of the lens. The energy is depicted along the vertical axis, in a relative scale, where for each aperture the maximum number is set to 1. The computer simulated light intensity distributions assume a biconvex lens body of an ophthalmic lens of the type shown in FIGS. 2a, 2b, designed for targeting a zero-order focal point at 20 diopter, D, and focal points for near and far vision at 21.675 D and 18.325 D, respectively, symmetrically positioned with respect to the zero order. Reference numeral 154 refers to diffraction order 0, providing a focal point for intermediate vision, reference numeral 155 refers to the focal point for far vision at 18.325 D and reference numeral 156 refers to the near vision focal point at 21.675 D. It can be seen in the graph the exact positions of these peaks vary slightly with aperture, as discussed elsewhere this effect can be purposely used in lens design.

A lens constructed in this manner provides a good Far even for very small pupils. There are two main drawbacks with a design like this. Firstly, Inserting the monofocal central zone to the diffraction grating reduces diffraction efficiency. Secondly, when using this architecture to provide full vision (including Far vision, intermediate vision and near vision) it is necessary to balance the intensity distribution to provide a desired intensity distribution for photopic conditions, e.g., an aperture diameter of 3 mm. For a trifocal lens this usually involves providing a stronger far vision compared to other distances, however with relatively strong near and some intermediate vision. Because of the skew towards near vision needed in the diffraction grating to make up for the strong far vision in the center such a design leads to a too strong relative near energy at larger apertures.

FIG. 5a shows a top view of an ophthalmic multifocal aphakic intraocular lens 50, working in accordance with the present invention, and FIG. 5b shows a side view of the lens 50. The difference over the prior art, exemplified in FIG. 2 are in the optics of the lens. The lens body 56 has a biconvex shape, comprising a front or anterior surface 54 and a rear or posterior surface 55. The skilled person would know that for some embodiments one or both of the anterior surface 54 and the posterior surface 55 might be concave or planar, depending on the refractive baseline needed for a specific application. In this application of the invention the lens body, in accordance with the present disclosure, comprises a peripheral lens portion 53 and a central lens portion 51 that is combined with a symmetric multifocal diffraction grating 52. The lens is constructed such that, for a design wavelength, one of the diffractive orders of the symmetric multifocal diffraction grating 52 contributes to the far vision of the lens, the $0^{th}$ order of the symmetric multifocal diffractive grating contributes to the intermediate vision of the lens, and yet another diffraction order contributes to near vision. In some embodiments the symmetric multifocal grating has three focal points, in other embodiments the number of focal points is a higher, odd, number, such as 5, 7, or 9. The central lens portion 51 has a dominant main optical power that is somewhere in between the powers of the intermediate and the far vision. FIGS. 5a and 5b shows a lens where one side of the lens is purely refractive, while the other side has a diffractive grating superpositioned over a refractive base line. As explained above in relation to FIG. 3, this is only one possible configuration. It is possible, for example, to distribute the diffractive grating over both sides, or super-position the diffractive grating to either side of a plano-convex or plano-concave lens. When a diffractive pattern is said to be combined with a refractive surface it can have either of these meanings.

The shape or height profile of the refractive baseline for any of the portions of the lens may be selected among a plurality of continuous refraction profiles known from monofocal lenses, such as spherical, or based on monofocal diffractive surface, or aspherical surfaces, which are among the most general known shapes of monofocal lenses known in the art. Monofocal diffractive surfaces refers to the phase-matched Fresnel lenses discussed earlier. By adjusting the phase matching number an arbitrarily wide unbroken monofocal zone can be created through diffractive optics. It is possible combine different types of refractive surfaces in one lens, so that the central portion and the peripheral portion consist of different types of refractive surfaces. The manufacturing of refractive of diffractive surfaces can be carried out by any of laser micro machining, diamond turning, 3D printing, or any other machining or lithographic surface processing technique, for example.

The present invention describes a way to create lens that maintains the advantages of the prior art lens in FIG. 4a and that increases diffraction efficiency and significantly increases the amount of light usable for the human eye.

This involves changes to two parts of the lens, the central portion of the lens, approximately within the 1 mm aperture, and the symmetric multifocal diffraction grating. By changing these two structures in concert we can arrive at the desired traits. FIG. 6 describes one such possible change to the central portion of the lens profile.

One very important property of a multifocal lens turns out to be the exact placement of the dominant optical power for very tiny apertures, e.g. as measured at 1 mm aperture. While FIG. 4*a* shows a lens profile where the optical power of the central zone perfectly aligns with one of the non-zero orders of symmetric multifocal diffractive grating, the central zone in FIG. 6*a* shows the profile of lens with a monofocal central zone that is slightly adjusted towards the $0^{th}$ order, used for intermediate vision. Exactly as in FIG. 4*a* as well as in PCT/EP2019/080758 a so-called transition point, as marked by the dashed vertical lines in the figure, around the peak closest to the optical axis (the optical axis passes in this image vertically through the center of the plotted lens profile).

A monofocal central zone adds a local negative optical power to the center of the lens, relative to a refractive baseline. In the prior art it was proscribed that this power should be identical to the absolute power of the diffractive order responsible for far vision. However, a slight shift of power in a monofocal central zone can be used to achieve a more favorable light distribution. It has been found that a small decrease of the power of the central zone can have several positive effects. (1) It increases, when chosen correctly, the overall diffraction efficiency and over all the portion of the light usable for the eye, (2) it decreases the intensity of the unusable light that has lower power than the intended far vision, (3) by broadening the peak of vision it broadens the landing zone, and is a way to choose the power at e.g. a 1 mm aperture. In some configuration it can produce an asymmetric peak for the focal point providing far vision. Especially the broadening of the landing zone (sweet spot) by slight shift of power towards stronger diopters for very small apertures can be important to increase the chance of clinical success.

In terms of the specific example present here, FIG. 6*b* shows the simulated relative intensity peaks for four different apertures. The power shift decreases the undesired peak, here present around 17 D, and redirects some of that light to the $0^{th}$ order (intermediate vision). The peak responsible for far vision can be found around 18.35 D. These features can be compared with FIG. 4*b*, where the most impactful change is the weakening of the undesired peak around 17 D in FIG. 6, meaning that more light is rendered useful for the eye.

The lens profile in FIG. 6*a* makes use of a diffraction grating that is identical to that of the lens in FIG. 4*a*, but in FIG. 6*a* the central zone has a negative power that is 0.275 D smaller in absolute terms. The symmetric diffraction grating is constructed to provide an order separation of 1.675 D. while the monofocal central zone has a curvature arranged to add a negative power to the refractive baseline of the lens that is 1.4 D. As simulated in FIG. 6*b* the dominant peak for a small 1 mm aperture is 1.2 D below the intended intermediate peak, rather than the 1.675 D of the nominal power of the diffraction order coinciding with far vision. This increases overall efficiency and broadens slightly peak for far vision. It is a tool that is very important and that is very useful when used in the right way.

A purely monofocal shape has been chosen for the central portion of these lenses because it is advantageous to have a very dominant far vision for small apertures and far vision that is at least stronger than the other for all larger apertures.

However, it is not necessary to use a purely monofocal zone to achieve this. FIGS. 7*a*, 7*b*, and 7*c* exemplify a different choice of central zone. It is advantageous to use a transition zone between the central portion and the diffraction grating that is located close to the peak of the first peak of the diffraction grating. FIG. 7*a* shows such a lens profile. The vertical dashed lines in FIG. 7*a* points out the transition point, corresponding to the center of the transition zone. To avoid a sudden change in the profile there is a smooth transition between the central portion, that is very geared towards the far vision, and the first ridges of the symmetric diffraction grating, which are fully trifocal and arranged to slightly favor near vision. This specific example is made in such a way that the smooth transition between the two zones is carried out in parameter space, rather than just adding a transition between two heights.

Such central portion, that is not purely monofocal, could be constructed as a aspheric lens segment, as a modified spherical segment or as several spherical segments stitched together. Additionally, it can be calculated through the same means used to calculate diffractive unit cells for the multifocal symmetric diffractive grating. Several different ways to create such unit cells are discussed earlier in this document. If the latter method is used it is often advantageous to create a unit cell that strongly promotes the diffractive focal point responsible for far vision and then use only a portion of that unit cell. The more it is skewed towards far vision, the more it can be made to resemble a purely monofocal lens portion. Near the correct position of the crest closest to the center of the lens it is then transitioned to a diffraction grating with a substantially different light distribution. It can be noted that for a lens like this with a nominal order separation of 1.675 D, as in the present example, the first grating period, counted from the lens center, would end at and aperture of 1.62 mm (0.81 mm distance from the center). This is a large portion of the lens and illustrates the fact that it needs to be constructed carefully and that it needs more than one feature to achieve the desired light distribution. In the present case the transition point is at an aperture of 1.25 mm and a unit cell like the one shown in FIG. 7*c* was used for the central zone. This shape is very strongly geared towards far vision (here arranged to coincide with the +1 order of the unit cell), as can be seen in the plot of the efficiency distribution of the unit cell in question. However, the portion between the two vertical dashed lines was not used. Instead, the optical axis of the lens roughly coincides with dashed line to the right in the image of the unit cell. The central portion of the lens then consists of roughly the portion of the unit cell shown not between the two dashed vertical lines. Around the vertical line to the left (close to the left shoulder of the unit cell) the lens data is created by transition in parameter space. It is of course also possible to make an abrupt transition between the central zone and the multifocal diffraction grating. A central zone such as the one exemplified in FIG. 7*a* is essentially monofocal, but with shape that is more similar to the diffractive grating, which increases total efficiency of the lens. This provides further opportunity to tune total efficiency and exact power of the peak at 1 mm aperture.

FIG. 7*b* shows the simulated relative intensity peaks for four different apertures. The symmetric diffraction grating is constructed to provide an order separation of 1.675 D. As simulated in FIG. 7*b* the dominant peak for a small 1 mm aperture is, however, only 0.65 D below the intended intermediate peak. The undesired peak at 17 D is here visibly smaller than corresponding peaks in FIGS. 4*b* and 6*b*, indicating higher efficiency for the lens in FIG. 7*a*. This higher efficiency is also clearly born out in simulation as well as measurements from actual lenses. However, this graph also very clearly states the main drawback of the lens of FIG. 7a: the high energy directed towards near vision for large apertures. At a 4.5 mm aperture the near energy is here much higher than that of intermediate vision and even similar in strength to that of far vision. Much of this near light from large apertures cannot be used by the eye. So even if the diffraction efficiency is high, the physiological light efficiency for large apertures is much lower than what is ideal. To solve this problem, what's needed is a fully adaptive lens.

FIG. 8 illustrates the respective activation of rods and cones in the eye. Because of luminance levels and the pupil diameters, cones are dominant in photopic conditions, whereas rods are dominant in mesopic and scotopic conditions.

Based on the specific response of cones and rods in the eye's retina, the main three modes of eye function under different illuminance levels $(cd/m^2)$, photopic (bright light), scotopic (low light conditions) and mesopic (intermediary) are observed. The brightness level of the object observed, the background and surroundings determine the activity of rods and cones by retinal illuminance level (light intensity). Therefore, eye spectral response is directly related, and influenced by illuminance levels to which it is exposed, as depicted in FIG. 8. Pupil size is a linear function of the log of equivalent luminance (log $cd/m^2$) calculated for large fields for adapting luminances from photopic to mesopic conditions (for further information, one may refer to: W. Adrian, "Spectral sensitivity of the pupillary system," Clin. Exp. Optom., vol. 86, no. 4, pp. 235-238, 2003).

Pupil size plays an important role in achieving functional vision levels in the pseudophakic eye, since the eye is not able to produce a refractive change in response to object proximity. Pupil diameter is the main predictor for increased pseudoaccommodation and near visual acuity, as well as reading performance by determining the retinal blur area and the depth-of-field (refer to: E. Fonseca, P. Fiadeiro, R. Gomes, A. S. Trancon, A. Baptista, and P. Serra, "Pupil function in pseudophakia: Proximal miosis behavior and optical influence," Photonics, vol. 6, no. 4, 2019).

Diffraction is the dominant limiting factor in small pupil diameters, while at large sizes, aberrations contribute more to retinal blur (referring to: A. Roorda and D. R. Williams, "The arrangement of the three cone classes in the living human eye," Nature, vol. 397, no. 6719, pp. 520-522, 1999). FIG. 9 shows the typical point spread function (PSF) of the eye as a function of pupil size. Studies have shown that the balance between diffraction (which blurs the image for small pupils) and aberrations (affecting the lateral resolution) is somewhere between 2 mm and 4 mm pupils, depending on the individual (See A. Roorda et al., "What can adaptive optics do for a scanning laser ophthalmoscope?", Bull. Soc. Belge Ophtalmol., no. 302, pp. 231-244, 2006). Larger aberrations for large pupils are yet another reason why light directed to near vision cannot be physiologically utilized.

FIG. 9 illustrates the point spread function (SPF) for different eyes and conditions. The top row shows the point spread function of an eye with no aberrations. As the pupil size increases the PSF decreases in size, offering the potential for higher resolution. The lower row shows the point spread functions for an eye with typical aberrations. In this case aberrations, particularly for the larger pupil sizes, blur the PSF.

Additionally, pupil size is a function of accommodation stimulus position for different ages (J. F. Zapata-Díaz, H. Radhakrishnan, W. N. Charman, and N. López-Gil, "Accommodation and age-dependent eye model based on in vivo measurements," J. Optom., vol. 12, no. 1, pp. 3-13, 2019). A correlation between maximum pupil size and age, represents a −0.23 mm reduction in distance pupil diameter per decade of life, so that individuals in their 50s show an average pupil of 5.0 mm and individuals in their 80s present a 4.1 mm average pupil (E. Fonseca, P. Fiadeiro, R. Gomes, A. S. Trancon, A. Baptista, and P. Serra, "Pupil function in pseudophakia: Proximal miosis behavior and optical influence," Photonics, vol. 6, no. 4, 2019).

The pupillary system ability to dilate can be reduced because of traumatic situations of the eye, such as cataract surgery. Therefore, a psuedophakic eye is less diluted than normal under scotopic, mesopic and photopic static illuminance conditions (referring to: H. K. Bhatia, S. Sharma, and P. Laxminarayana, "Ophthalmology and Clinical Research Report Clin Med International Library," pp. 2-5, 2015, and A. J. Kanellopoulos, G. Asimellis, and S. Georgiadou, "Digital pupillometry and centroid shift changes after cataract surgery," J. Cataract Refract. Surg., vol. 41, no. 2, pp. 408-414, 2015). Postoperative pupil diameter is reduced by approximately −0.3 mm compared to preoperative measurements (A. J. Kanellopoulos and G. Asimellis, "Clear-cornea cataract surgery: Pupil size and shape changes, Along with anterior chamber volume and depth changes. A Scheimpflug imaging study," Clin. Ophthalmol., vol. 8, pp. 2141-2151, 2014.)

Additionally, measurement conditions can affect the level of retinal illuminance. Most scientific research is based on monocular pupillometry, where in reality an IOL performance should be evaluated for binocular vision. The binocular dynamic pupillometer is necessary to accurately determine pupil size under binocular conditions. It is known that light stimuli bring about more contraction to the pupil rather than monocular vision, since the indirect reflection of the pupillary system in binocular conditions is added to the direct reflection for single eye stimulation.

Surgeons can predict the postoperative pupil size, affecting the refractive outcomes and subsequent patient satisfaction after cataract surgery, if they can accurately and reproducibly determine the preoperative pupil size. This is the basics of pupil-customized cataract surgery (PCCS) which means predicting and maximizing the postoperative visual performance and subsequent patient satisfaction by the preoperative assessment of pupil size in cataract patients (for further information see Cataract surgery: Maximizing outcomes through research by H. Bissen-Miyajima, M. P. Weikert, and D. D. Koch, published in 2014).

As has already been discussed hitherto, the visual system is more sensitive to light coming in through the center of the eye pupil than to light entering from the periphery of the pupil due to the SCE. The SCE can significantly improve defocused image quality and defocused vision, particularly for tasks that require veridical phase perception.

These findings may be used clinically in assessing visual performance after cataract surgery and may have significance in terms of IOL design. Diffractive multifocal intraocular lenses provide vision for far, Intermediate, and near vision. The ideal energy distribution between them differs for different pupil sizes. For small pupils the dominating focus should be at far vision with a slightly stronger optical power than Far. For pupil sizes of around 3 mm the ideal diffractive multifocal lens should provide strong far vision, strong fear vision, and some intermediate vision. For pupils larger than 4.5 mm energy directed to near vision cannot not be used well by the eye. Because of this, as little additional energy as possible should be directed to near and the energy going to near for 4.5 mm pupil should be less than for both intermediate and near.

Therefore, multifocal intraocular lenses should ideally distribute the light energy between the foci in a way that in mesopic illuminance levels, nearly 80% of the light energy is directed to the far and near vision, while in scotopic illuminance levels, this nearly 80% of the light energy should ideally be distributed to the far and intermediate vision.

FIG. 10a shows an example of a lens according to the present invention. To obtain a fully adaptive lens the intensity distribution of the diffractive grating should change as a function of the distance from the optical center. FIG. 10a shows a lens profile, less the refractive baseline, that uses a central zone that is substantially concave and promotes far vision very strongly but is tuned to harmonize better with the multifocal grating of the lens. A transition point at an aperture of 1.25 mm, around the first peak leads into a symmetric multifocal grating consisting of a set of differently tuned diffractive unit cells. The first periods outside of the central portion constitute a relatively balanced diffractive grating that promotes near vision more than intermediate and far, this is then with increasing distance from the optical center transitioned over several steps to a diffractive grating that promotes far strongly, and especially disfavors near vision with regards to both far and intermediate vision. It is of course the case, that even if near vision is slightly favored in the region of the lens in between the central portion and approximately the 3 mm apertures, far vision has for all pupil size in this range the dominant intensity share, because of the far promoting central portion.

It is of course possible and often useful, to create an adaptive lens that has a fully monofocal central zone, such as in FIG. 6a. In such a configuration you have an adaptive lens with a strictly defined focal point for all diameters smaller than that of the transition point. Adaptive lenses using strictly monofocal central zones have slightly lower overall light efficiency compared to the type of lens described in FIG. 10, however, lens designs with the strictly monofocal central zone have practically been shown to be more robust in response to manufacturing and material perturbations. Material perturbations can be slight difference in refractive index between material batches. Monofocal central zones can also have some advantages for postoperative autorefractometer measurements. Because of these reasons the choice of central zone will have to be done on a case-by-case basis.

FIG. 10b shows the simulated relative intensity peaks for four different apertures. The symmetric diffraction grating is nominally constructed to provide an order separation of 1.675 D. As shown in the simulation data the dominant peak for a small 1 mm aperture is, however, only 0.6 D below the intended intermediate peak. To summarize the data in FIG. 10b, we see here that (1) the dominant focus at the 1 mm aperture is placed in between far and intermediate powers (18.32 D and 20 D, respectively), (2) the portion of energy directed to near vision (at about 21.7 D) is higher at 3 mm than at any of the other shown apertures, the intermediate energy is (3) at the 2 mm aperture weaker than both far and near, while (4) at 4.5 mm the near intensity is weaker than far as well as intermediate. At all apertures from 2 mm and above far is the strongest type of vision.

To create an adaptive diffractive lens according to the present invention it is necessary to use diffraction efficiencies that changes as a function of aperture. FIGS. 10c, 10d, and 10e show examples of underlying linear grating diffractive unit cells and their respective diffraction efficiencies. The efficiencies are calculated with standard methods from linear grating profile data. This diffraction efficiency calculation can of course be carried out on any arbitrarily unit cell of any shape. In this specific lens and with used conventions it is arranged so that the −1 order corresponds to light arranged for Near vision, $0^{th}$ order corresponds to light arranged for intermediate vision, and +1 order corresponds to light arrange for far vision. The total diffraction efficiency given for each of these three figures is the sum of the diffraction efficiencies of the three desired diffraction orders. FIG. 10c shows the diffractive efficiencies of the profile shape used in the lens portion marked as G1 in FIG. 10a. Near vision is promoted in favor of other depths, while those of far and intermediate are kept similar. FIG. 10d shows the diffractive efficiencies of the profile shape used in the lens portion marked as G2 in FIG. 10a. Far vision is here promoted in favor of other depths, but especially light distributed to near vision is kept very low. FIG. 10e shows the diffractive efficiencies of the profile shape used in the lens portion marked as G3 in FIG. 10a. Here energy distributed to far and intermediate vision are kept relatively similar, while additional near light is kept very low. For large apertures, essentially apertures above 4.5 mm there is very small to no benefit of intensity provided to near vision. The limit on the gratings and/or refractive shapes used here comes down to undesired effects. As is discussed further below it is possible to construct an adaptive lens according to the present invention with e.g., a peripheral, bifocal sawtooth grating or peripheral portion with a refractive power corresponding to far vision. These are two examples of ways to reduce additional intensity to near vision to essentially zero. Of course, they can confer negative optical properties, such as glare and halo effects.

It is important to understand that these unit cells are specific examples. In the lens shown in FIG. 10a several more different unit cells are present. It is often advantageous to slowly progress the relative intensity distributions as a function of aperture. It is possible to use unit cells with very different diffractions efficiencies and resulting energy distributions than those shown in this example.

FIG. 11a shows another lens diffractive profile according to the disclosed invention and demonstrates one additional way to change the dominant power of the central portion of the lens. In FIG. 6a a lens profile is demonstrated where the dominant power at small apertures was tuned by changing the curvature of the central zone. The placement of the dominant optical power at small apertures, such as 1 mm, can also be tuned very carefully by horizontal shifting of the central profile (that is, in a direction normal to the optical axis) of the central portion. The lens profile in FIG. 11a is, except for this horizontal shift, identical to the profile shown in FIG. 10a up to an aperture of approximately 2.4 mm. FIG. 11b shows the simulated relative intensity peaks for four different apertures. It is meaningful to compare this model data with the data in the FIG. 10b. Because of this relatively small change in the profile of FIG. 11a the dominant peak at 1 mm is moved approximately 0.8 D closer to the power intended for far vision. This arrangement lowers overall efficiency slightly, as calculated over the full range of vision, but it provides a stronger far vision. It further provides for very tiny apertures a dominant power that is close to that of the intended far power, which can be advantageous in some circumstances, for examples for some methods to measure eye power post operatively.

One additional change between the lens profiles in FIGS. 10a and 11a, respectively, is that the latter exhibits a higher diffractive lens profile outside of approximately apertures of 2.4 mm. This portion of the lens is here geared towards increasing intensity directed towards far vision more strongly for very large apertures. One possible design choice if even stronger weakening of near light for large apertures would be desired is to make use of a bifocal sawtooth grating for example for apertures larger than 4.5 mm. Such a bifocal sawtooth grating could be arranged to provide additional light only for far and intermediate vision. Yet another option would be to use a monofocal sawtooth structure for large apertures. Such a structure would then need to be much higher than the multifocal gratings.

It should be further noted that the central portion, up to around the crest closest to the lens center, and the diffraction grating are separable and that a small horizontal shift of the central portion doesn't have to be joined by an equal shift of the diffractive grating. Likewise, a shift of the diffraction grating does not have to joined by an equal shift of the central zone. On the contrary, it can often be advantageous to shift the central portion and the diffraction grating relative to each other. Specifically, it can often be advantageous to perform a shift so that the ridge closest to the lens center is thinner than typically expected by the formula for a well-formed lens. A different way to phrase this is to say that it is often found to be advantageous to move the central zone and the first trough of the diffractive grating closer to each other than expected from the standard formula for Fresnel zone plates. Such a configuration can increase overall light efficiency and is a viable way to construct a lens according to the present invention.

FIG. 12a shows yet another lens profile for an adaptive multifocal lens according to the present invention. It is important to understand that the profile in shown here is less the refractive base line, understood to be the same over the whole optic. One important feature of this lens profile is that it contains a purely refractive portion that is arranged to provide light for far vision only. In this example this refractive portion covers roughly all apertures outside of the 5 mm aperture. Such refractive portions should not be considered when peak-to-peak height of the diffractive profile is calculated. Having a refractive portion at the periphery of a multifocal lens can be a good way to create a strongly adaptive lens. In the present case all light will be directed towards far vision for apertures larger than 5 mm. It could increase the risk of halo effects.

A second important feature of the diffractive lens profile in FIG. 12a is a purely monofocal center. In this example the central zone is formed to have a negative power that is 0.125 D lower than the nominal absolute difference between the orders responsible for far and intermediate power. The transition point between the central zone and the symmetric multifocal diffraction grating is marked by the vertical, dashed line at an aperture of 1.14 mm. The symmetric diffraction grating is constructed in a fashion that is relatively similar to the one depicted in FIG. 10a. The diffraction grating is geared towards near vision until an aperture of about 2.8 mm, then it is with increasing aperture tune more and more strongly for far, and to some extent intermediate vision.

FIG. 12b shows the simulated relative intensity peaks for four different apertures. The symmetric diffraction grating is nominally constructed to provide an order separation of 1.675 D. As shown in the simulation data the dominant peak for a small 1 mm aperture is 1.4 D below the intended intermediate peak. To summarize the data in FIG. 12b, we see here that (1) the dominant focus at the 1 mm aperture is placed in between intended far and intermediate powers (18.32 D and 20 D, respectively), (2) intensity of near, relative to that of far intensity, is stronger at 3 mm than at any of the other shown apertures, the intermediate intensity (3) is at the 2 mm aperture weaker than both far and near, while (4) at 4.5 mm the near intensity is weaker than far as well as intermediate. At all apertures from 2 mm and above far is the strongest type of vision. The undesired peak around 17 D is larger than e.g. the peak shown in FIG. 10b, this is due to the choice of central zone.

FIG. 13a is an illustration of what is a possible goal energy distribution for lens designs according to the patent. This ideal distribution for an adaptive diffractive multifocal lens is based on the arguments of workings of the human eye earlier in this document. The illustration indicates for each of near, intermediate, and far vision the desired energy distribution at apertures up to 6 mm. It can be assumed that values within ±5 percentage points are within the ideal region. Often a lens made according to the present invention will not fall into the ideal region for all types of vision nor for all apertures. Further, it should be noted that this demonstrates an ideal outcome, only taking the energy distribution into consideration. Especially the very dramatic exchange of near energy with intermediate energy when going from a mesopic pupil to a scotopic pupil is difficult realize fully. When making a design of a lens according to the present invention it is often necessary to take into consideration if the main prioritization for the peripheral part of that specific design should be correct energy distribution or if minimization of aberrations and undesired photic phenomena should be prioritized. Very efficient ways to change the energy distribution for large apertures include bifocal sawtooth gratings and purely monofocal zones. For example, the bifocal sawtooth grating could be arranged to provide only light for far and intermediate vision for large apertures. A peripheral monofocal zone, as illustrated in FIG. 12a, can be arranged to provide light for far vision only. However, both these structures can increase the risk of unwanted photic phenomena, especially halo effects.

FIG. 13b shows, as a function of aperture, the simulated energy distribution between far, intermediate, and near vision for the hybrid lens in FIG. 10a. The aperture is here seen as simply double the lens radius. In this simulation far vision is dominant at all apertures, at an aperture of 2 mm energies for near and intermediate vision are relatively similar. Near energy has a maximum plateau for apertures 2.5 mm to 3 mm, while intermediate energy has a minimum plateau for approximately the same aperture range. For apertures larger than 3.1 mm near energy is decreasing with increasing apertures, while intermediate energy is increasing with increasing aperture. The cross-over point is estimated to be close to the 4.5 mm aperture. The data in the graph is composed by first calculating the spectrum at 8 apertures per period of the diffractive grating, all in all at 105 different apertures. For each aperture the intensity of each vision is approximated with the local maximum peak in the in the position of respective type of vision. The graph is then plotted using the sliding mean values for each type of vision, using for each point in the graph data for a whole period. A less undulating line would be arrived at if calculations were made at e.g., only troughs or crests.

Other variations to the disclosed examples and embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope thereof. Same reference signs refer to equal or equivalent elements or operations.

According to the disclosed invention, an ophthalmic multifocal lens, arranged to provide far, intermediate, and near vision, said lens having a light transmissive lens body with an optical axis and a refractive baseline that extends over at least a part of the lens body, said lens further having a first portion that coincides with a central area of said light transmissive lens body, extending concentrically in a radial direction, and a multifocal second portion, extending concentrically in a radial direction is proposed.

According to an embodiment of the disclosed invention, said second portion of the ophthalmic multifocal lens further comprises a symmetric multifocal diffractive grating super-positioned onto said refractive baseline, covering a portion of the lens, its shape and resulting light intensity distribution thereof changing with respect to its distance to the optical axis.

According to an embodiment of the disclosed invention, said first portion of said ophthalmic lens is configured so that super positioned onto said refractive baseline around the optical axis is a substantially concave shape, connected to the ridge of said symmetric multifocal diffractive grating that is closest to the optical axis.

According to an embodiment of the disclosed invention, said refractive baseline provides a focal point substantially coinciding with the intermediate power.

According to an embodiment of the disclosed invention, said first portion of said ophthalmic lens is configured to provide a dominant optical power that is in between the intended powers of far vision and intermediate vision, such that the monofocal central zone has a curvature arranged to add a negative power to the refractive baseline of the lens.

According to an embodiment of the disclosed invention, said embodiments disclosed hitherto provide a transition zone between the central portion and the diffraction grating that is located close to the peak of the first peak of the diffraction grating.

According to an embodiment of the disclosed invention, said ophthalmic multifocal lens is configured to have a ratio of energy intended for far vision to energy intended for near vision that is lower for an aperture of 3 mm compared to same ratio for apertures of 2 mm and 4.5 mm.

According to an embodiment of the disclosed invention, said ophthalmic multifocal lens is configured such that for an aperture of 5 mm, energy intended for near vision is weaker than energy intended for intermediate and far vision, respectively, and said ophthalmic multifocal lens is configured such that for an aperture of 3 mm, intermediate energy is weaker than both the near and far energies.

According to an embodiment of the disclosed invention, said ophthalmic multifocal lens is configured such that, for a 3-mm aperture, modulation transfer function ratio of far vision to near vision is lower than that for 2- and 4.5-mm apertures, measured at 50 lines per millimeter.

According to an embodiment of the disclosed invention, said symmetric multifocal diffraction grating further comprises a wave-type diffraction pattern, comprising alternating crest and trough amplitude values, whereby said first portion is concave from a point coinciding with the optical axis of the lens and up to a point that is configured to be of greater proximity to a crest amplitude value than that of a trough amplitude as measured along a direction normal to the optical axis.

According to an embodiment of the disclosed invention, the power difference of intermediate and far vision is configured to be between 1.5 D and 2.2 D, whereas the power difference of far and near vision is configured to be between 3 D and 4.4 D.

According to an embodiment of the disclosed invention, said first portion comprises a shape arranged for monofocality.

According to an embodiment of the disclosed invention, said symmetric multifocal diffraction grating provides a number of focal points that is selected from a group including, but not limited to, three, five, seven, nine focal points.

According to an embodiment of the disclosed invention, at least one of said first portion, said second portion, or both said portions are combined with a sawtooth diffractive grating that is substantially monofocal for a design wavelength.

According to an embodiment of the disclosed invention, for apertures larger than 3.5 mm the lens comprises at least one optically active feature from a group including, but not limited to, an asymmetric diffractive grating, a shape providing refractive power other than that of said refractive baseline, a symmetric diffractive grating with an odd number of focal points that is different from that of said symmetric multifocal diffractive grating.

According to an embodiment of the disclosed invention, said symmetric multifocal diffraction grating comprises within the 4.5 mm aperture at least two periods of said symmetric multifocal grating having the relation that, for the corresponding linear grating unit cells, the diffraction efficiency for an order responsible for near vision is at least ten percent higher for the period of the two periods that is located closest to the optical axis compared to the period located further from the optical axis.

According to an embodiment of the disclosed invention, the highest point of the crest closest to the optical axis of said multifocal grating is placed at a normal distance from the optical axis within the range of 0.45 mm to 0.73 mm.

According to an embodiment of the disclosed invention, the point of said first portion coinciding with the optical axis of said multifocal lens is configured to be lower compared to said refractive baseline than any other trough within the central 3 mm of said multifocal lens.

According to an embodiment of the disclosed invention, the maximum peak-to-peak height of said symmetric multifocal diffraction grating is, for a design wavelength, less than 50 percent of full phase modulation, calculated such that the trough of said first portion is omitted.

According to an embodiment of the disclosed invention, said lens when measured with a concentric 1-mm aperture has a dominating power that is between the intended far and intermediate powers.

According to an embodiment of the disclosed invention, said lens, when measured with a concentric 1-mm aperture, has a dominating power that is not more than 1.2 D stronger than the intended power for far vision.

According to at least one embodiment of the disclosed invention, an ophthalmic multifocal lens, comprising at least three focal points, providing light for near, intermediate and far vision is proposed.

According to at least one embodiment of the disclosed invention, multifocality of the lens is provided by a multifocal symmetric grating superpositioned on top of a refractive baseline.

According to at least one embodiment of the disclosed invention, said multifocal symmetric grating covers a contiguous portion of the lens, which may cover the whole optic portion, or a part smaller than that.

According to at least one embodiment of the disclosed invention, said multifocal symmetric grating differs in terms of shape and intensity distribution as a function of the distance to the optical axis.

According to at least one embodiment of the disclosed invention, said lens has a central zone providing a dominant peak of a power that is less than 1.2D stronger than the intended far power of said lens.

According to at least one embodiment of the disclosed invention, said central zone is, less the baseline curvature, a concave shape that is connected to a multifocal diffractive grating at a transition point.

According to at least one embodiment of the disclosed invention, a ratio of the far energy to near energy is lower for a 3 mm aperture than for apertures of 2 mm, as well as 4.5 mm.

According to at least one embodiment of the disclosed invention, for a 3 mm aperture, intermediate energy is weaker than that of both far and near visions.

According to at least one embodiment of the disclosed invention, the modulation transfer function (MTF) of Far vision is at least 35% higher than that of Near vision, and at least 20% higher than that of intermediate vision measured at 50 and 100 lines per millimeter for apertures between 1.5 mm to 6 mm.

According to at least one embodiment of the disclosed invention, the MTF-ratio of Far to Near is lower for a 3 mm aperture than for apertures of 2 mm, as well as 4.5 mm.

According to at least one embodiment of the disclosed invention, said diffraction grating comprises a wave type diffraction pattern, having alternating crest and trough amplitude values, said transition point being located closer to a crest amplitude value than a trough amplitude value of said diffraction grating.

According to at least one embodiment of the disclosed invention, addition power values for intermediate is 1.5 D to 2.2 D and for near focus is between 3 D to 4.4 D.

According to at least one embodiment of the disclosed invention, troughs of each period of said multifocal symmetric diffraction grating is aligned with the refractive baseline.

According to at least one embodiment of the disclosed invention, said central zone comprises a monofocal zone.

According to at least one embodiment of the disclosed invention, said multifocal lens is a trifocal lens and as such said multifocal symmetric grating provides three focal points.

According to at least one embodiment of the disclosed invention, said multifocal symmetric grating provides a number of focal points selected from a group including, but not limited to, four, five, seven, nine focal points.

According to at least one embodiment of the disclosed invention, said multifocal symmetric grating comprises at least two diffractive cells that have significantly different shape from one another.

According to at least one embodiment of the disclosed invention, said multifocal symmetric grating comprises at least a first and a second portion where the diffraction efficiency for the order responsible for Near vision is at least 30% higher in the first portion than in the second.

According to at least one embodiment of the disclosed invention, said central zone has a diameter that is between 0.9 mm to 1.4 mm.

According to at least one embodiment of the disclosed invention, the maximum peak-to-peak height of said multifocal symmetric grating is less than 80% of full phase modulation and preferably less than 50% of full phase modulation.

According to at least one embodiment of the disclosed invention, diffraction gratings outside of said central zone is placed close to the central zone than that for a diffractive lens that follows the spacing of a well-formed Fresnel lens.

The invention claimed is:

1. An ophthalmic multifocal lens, arranged to provide far, intermediate, and near vision, comprising a contact lens or an intraocular lens, said lens having a light transmissive lens body with an optical axis and a refractive baseline that extends over at least a part of the lens body, said lens further having a first portion that coincides with a central area of said light transmissive lens body, extending concentrically in a radial direction, and a multifocal second portion, extending concentrically in a radial direction, wherein said second portion of the ophthalmic multifocal lens further comprises a symmetric multifocal diffractive grating super positioned onto said refractive baseline, covering a portion of the lens, its shape and resulting light intensity distribution thereof changing with respect to its distance to the optical axis, said symmetric multifocal grating at least comprising one diffractive order contributing to far vision and one diffractive order contributing to near vision, a 0th order of said symmetric multifocal diffractive grating super positioned onto said refractive baseline substantially coincides with the power of the refractive baseline as well as an intended intermediate power of the lens, said first portion of said ophthalmic lens is configured so that super positioned onto said refractive baseline around the optical axis is a substantially concave shape, connected to the ridge of said symmetric multifocal diffractive grating that is closest to the optical axis, said refractive baseline provides a focal point substantially coinciding with the intermediate power, and;

said first portion of said ophthalmic lens is configured to provide a dominant optical power that is in between the intended powers of far vision and intermediate vision, said ophthalmic multifocal lens is further configured such that;

for an aperture of 5 millimeters, energy intended for near vision is weaker than energy intended for both intermediate and far vision respectively;

for an aperture of 3 millimeters, intermediate energy is weaker than both the near and far energies respectively; and a ratio of energy intended for far vision to energy intended for near vision that is lower for an aperture of 3 mm compared to same ratio for apertures of 2 mm and 4.5 mm.

2. The ophthalmic multifocal lens, arranged to provide far, intermediate, and near vision as set forth in claim 1, wherein said ophthalmic multifocal lens is configured such that, for a 3-mm aperture, modulation transfer function ratio of far vision to near vision is lower than that for 2- and 4.5-mm apertures, measured at 50 lines per millimeter.

3. The ophthalmic multifocal lens, arranged to provide far, intermediate, and near vision as set forth in claim 1, wherein said symmetric multifocal diffraction grating further comprises a wave-type diffraction pattern, comprising alternating crest and trough amplitude values, whereby said first portion is concave from a point coinciding with the optical axis of the lens and up to a point that is configured to be of greater proximity to a crest amplitude value than that of a trough amplitude as measured along a direction normal to the optical axis.

4. The ophthalmic multifocal lens, arranged to provide far, intermediate, and near vision as set forth in claim 1, wherein the power difference of intermediate and far vision is configured to be between 1.5 D and 2.2 D, whereas the power difference of far and near vision is configured to be between 3 D and 4.4 D.

5. The ophthalmic multifocal lens, arranged to provide far, intermediate, and near vision as set forth in claim 1, wherein said first portion comprises a shape arranged for monofocality.

6. The ophthalmic multifocal lens, arranged to provide far, intermediate, and near vision as set forth in claim 1, wherein said symmetric multifocal diffraction grating provides a number of focal points that is selected from a group including, but not limited to, three, five, seven, and nine focal points.

7. The ophthalmic multifocal lens, arranged to provide far, intermediate, and near vision as set forth in claim 1, wherein at least one of said first portion, said second portion, or both said portions are combined with a sawtooth diffractive grating that is substantially monofocal for a design wavelength.

8. The ophthalmic multifocal lens, arranged to provide far, intermediate, and near vision as set forth in claim 1, wherein for apertures larger than 3.5 mm the lens comprises at least one optically active feature from a group including, but not limited to, an asymmetric diffractive grating, a shape providing refractive power other than that of said refractive baseline, and a symmetric diffractive grating with an odd number of focal points that is different from that of said symmetric multifocal diffractive grating.

9. The ophthalmic multifocal lens, arranged to provide far, intermediate, and near vision as set forth in claim 1, wherein said symmetric multifocal diffraction grating comprises within the 4.5 mm aperture at least two periods of said symmetric multifocal grating having the relation that, for the corresponding linear grating unit cells, the diffraction efficiency for an order responsible for near vision is at least ten percent higher for the period of the two periods that is located closest to the optical axis compared to the period located further from the optical axis.

10. The ophthalmic multifocal lens, arranged to provide far, intermediate, and near vision as set forth in claim 1, wherein a highest point, relative to said refractive baseline, of the crest closest to the optical axis of said multifocal grating is placed at a normal distance from the optical axis within the range of 0.47 mm to 0.75 mm.

11. The ophthalmic multifocal lens, arranged to provide far, intermediate, and near vision as set forth in claim 1, wherein a point of said first portion coinciding with the optical axis of said multifocal lens is configured to be lower compared to said refractive baseline than any other trough within the central 3 mm of said multifocal lens.

12. The ophthalmic multifocal lens, arranged to provide far, intermediate, and near vision as set forth in claim 1, wherein a maximum peak-to-peak height of said symmetric multifocal diffraction grating is, for a design wavelength, less than 50 percent of full phase modulation, calculated such that the trough of said first portion is omitted.

13. The ophthalmic multifocal lens, arranged to provide far, intermediate, and near vision as set forth in claim 1, wherein said lens when measured with a concentric 1-mm aperture has a dominating power that is between the intended far and intermediate powers.

14. The ophthalmic multifocal lens, arranged to provide far, intermediate, and near vision as set forth in claim 13, wherein said lens when measured with a concentric 1-mm aperture has a dominating power that is stronger than the intended power for far vision by at least 0.2 D, but not more than 1.2 D.

* * * * *